(12) United States Patent
Basset et al.

(10) Patent No.: US 6,184,256 B1
(45) Date of Patent: Feb. 6, 2001

(54) METHODS AND COMPOSITIONS FOR USE IN MODULATING EXPRESSION OF MATRIX METALLOPROTEINASE GENES

(75) Inventors: Paul Basset; Patrick Anglard; Eric Guérin, all of Strasbourg (FR)

(73) Assignees: Institut National de la Santé de la Recherche Médicale; Centre National de la Recherche Scientifique, both of Paris; Université Louis Pasteur, Strasbourg, all of (FR); Bristol-Myers Squibb Company, Princeton, NJ (US)

( * ) Notice: Under 35 U.S.C. 154(b), the term of this patent shall be extended for 0 days.

(21) Appl. No.: 09/065,904

(22) Filed: Apr. 24, 1998

Related U.S. Application Data

(60) Provisional application No. 60/044,258, filed on Apr. 24, 1997.

(51) Int. Cl.$^7$ .................................................. A61K 31/07

(52) U.S. Cl. ............................................................ 514/725

(58) Field of Search ............................................. 514/725

(56) References Cited

U.S. PATENT DOCUMENTS

| | | | |
|---|---|---|---|
| 5,399,586 | 3/1995 | Davies et al. | 514/448 |
| 5,702,914 | 12/1997 | Evans et al. | 435/29 |
| 5,747,661 | 5/1998 | Evans et al. | 536/24.1 |
| 5,780,676 | 7/1998 | Boehm et al. | 562/490 |
| 5,861,274 | 1/1999 | Evans et al. | 435/69.1 |

FOREIGN PATENT DOCUMENTS

| | | |
|---|---|---|
| 90 58248 | 12/1990 | (AU) . |
| 2057049 | 11/1990 | (CA) . |
| 2100582 | 9/1992 | (CA) . |
| 2210248 | 7/1996 | (CA) . |
| 2218955 | 10/1996 | (CA) . |
| 2230637 | 3/1997 | (CA) . |
| 0 325 849 B1 | 7/1995 | (EP) . |
| 0 479 916 B1 | 11/1996 | (EP) . |
| 0 502 979 B1 | 1/1997 | (EP) . |
| WO 95 04036 | 2/1995 | (WO) . |
| WO 95/18380 | 7/1995 | (WO) . |
| WO 96/01317 | 1/1996 | (WO) . |
| WO 96 33716 | 10/1996 | (WO) . |
| WO 97/09418 | 3/1997 | (WO) . |
| WO 97/35195 | 9/1997 | (WO) . |
| WO 98/29113 | 7/1998 | (WO) . |
| WO 98/29120 | 7/1998 | (WO) . |
| WO 98/48825 | 11/1998 | (WO) . |
| WO 98/49555 | 11/1998 | (WO) . |
| WO 99/05292 | 2/1999 | (WO) . |

OTHER PUBLICATIONS

Takeshita et al. (May 1996) Successful treatment of relapse of acute promyelocytic leukemia with a new synthetic retinoid, Am80. Ann. Internal Med. 124:893–896.*

Kuwabara et al. (Jan. 1996) Novel synthetic retinoic acid inhibits rat collagen arthritis and differentially affects serum immunoglobulin subclass levels. FEBS Lett. 378:153–156.*

Dialog File 351, Derwent World Patents Index, English language abstract for WO 99/05292 (Document AP4), WPI Accession No. 99–142944/199912.

Abrams, J.S., et al., "New Chemotherapeutic Agents for Breast Cancer," *Supp. Cancer* 74:1164–1176 (1994).

Anglard, P., et al., "Structure and Promoter Characterization of the Human Stromelysin–3 Gene," *J. Biol. Chem.* 270:20337–20344 (1995).

Apfelt, C.M., et al., "Enhancement of HL–60 Differentiation by a New Class of Retinoids with Selective Activity on Retinoid X Receptor," *J. Biol. Chem.* 270:30765–30772 (1995).

Basset, P., et al., "A novel metalloproteinase gene specifically expressed in stromal cells of breast carcinomas," *Nature* 348:699–704 (1990).

Beckett, R.P., "Recent advances in the field of matrix metalloproteinase inhibitors," *Exp. Opin. Ther. Patents* 6:1305–1315 (1996).

Clifford, J., et al., "RXRα–null F9 embryonal carcinoma cells are resistant to the differentiation, anti–proliferative and apoptic effects of retinoids," *EMBO J.* 15:4142–4155 (1996).

Durand, B., et al., "Activation function 2 (AF–2) of retinoic acid receptor and 9–cis retinoic acid receptor: presence of a conserved autonomous constitutive activating domain and influence of the nature of the response element in AF–2 activity," *EMBO J* 13:5370–5382 (1994).

Fanjul, A., et al., "A new class of retinoids with selective inhibition of AP–1 inhibits proliferation," *Lett. Nature* 372:107–111 (1994).

Hembry, R.M., et al., "Rabbit Models of Arthritis: Immunolocalization of Matrix Metalloproteinases and Tissue Inhibitor of Metalloproteinase in Synovium and Cartilage," *Amer. J. Path.* 143:628–642 (1993).

(List continued on next page.)

Primary Examiner—Robert A. Schwartzman
(74) Attorney, Agent, or Firm—Sterne, Kessler, Goldstein & Fox, P.L.L.C.

(57) ABSTRACT

The present invention relates to methods for identifying and selecting compositions useful in differentially modulating the expression of two or more mammalian genes, particularly matrix metalloproteinase (MMP) genes such as those encoding interstitial collagenase (and other genes comprising an AP1-binding site) and stromelysin-3 (and other genes comprising a retinoic acid response element (RARE)). In addition, the invention relates to methods of treating a mammal (such as a human) suffering from or predisposed to a physical disorder, using pharmaceutical compositions comprising the compositions identified or selected by the above-described methods. The methods of the present invention are useful in treating a variety of physical disorders in mammals including cancers (particularly carcinomas), inflammatory disorders, fibrotic disorders, ocular disorders and osteoporosis.

23 Claims, 10 Drawing Sheets

OTHER PUBLICATIONS

Horn, V., et al., "RAR and RXR selective ligands cooperatively induce apoptosis and neuronal differentiation in P19 embryonal carcinoma cells," *FASEB J. 10*:1071–1077 (1996).

Lafyatis, R., et al., "Interleukin–1 Stimulates and All–Tran–Retinoic Acid Inhibits Collagenase Gene Expression through Its 5' Activator Protein–1–Binding Site," *Mol. Endo. 4*:973–980 (1990).

Lehmann, J.M., et al., "Retinoids Selective for Retinoid X Receptor Response Pathways," *Science 258*:1944–1946 (1992).

Lotan, R., et al., "Enhanced Efficacy of Combinations of Retinoic Acid– and Retinoid X Receptor–selective Retinoids and α–Interferon in Inhibition of Cervical Carcinoma Cell Proliferation," *Can. Res. 55*:232–236 (1995).

Murphy, G., "Matrix metalloproteinases and their inhibitors," *Acta. Orthop. Scand. 66*:55–60 (1995).

Nicholson, R.C., et al., "Negatively regulation of the rat stromelysin gene promoter by retinoic acid is mediated by an AP1 binding site," *EMBO J. 9*:4443–4454 (1990).

Rouyer, N., et al., "Stromelysin–3 Gene Expression in Human Cancer: An Overview," *Inv. Metas. 14*:269–275 (1994).

Roy, B., et al., "Synergistic Activation of Retinoic Acid (RA)–Responsive Genes and Induction of Embryonal Carcinoma Cell Differentiation by an RA Receptor α (RARα)–, RARβ–, RARγ–Selective Ligand in Combination with a Retinoid X Receptor–Specific Ligand," *Molec. Cell Biol. 15*:6481–6487 (1995).

Sato, H., et al., "A matrix metalloproteinase expressed on the surface of invasive tumour cells," *Lett,. Nature 370*:61–65 (1994).

Taneja, R., et al., "Cell–type and promoter–context dependent retinoic acid receptor (RAR) redundancies for RARβ2 and Hoxa–1 activation in F9 and P19 cells can be artefactually generated by gene knockouts," *Proc. Natl. Acad. Sci. USA 93*:6197–6202 (1996).

Wolf, C., et al., "Stromelysin 3 belongs to a subgroup of proteinases expressed in breast carcinoma fibroblastic cells and possibly implicated in tumor progression," *Proc. Natl. ACad. Sci. USA 90*:1843–1847 (1993).

Yang–Yen, H.–F., et al., "Antagonism Between Retinoic Acid Receptors and AP–1: Implications for Tumor Promotion and Inflammation," *New Biologist 3*:1206–1219 (1991).

Chandraratna, R.A.S., et al., "Development of RAR subtype selective retinoids for dermatological diseases," *Eur. J. Med. Chem. 30*:505s–517s (1995).

Chen, J.–Y., et al. "RAR–specific agonist/antagonists which dissociate transactivation and AP1 transrepression inhibit anchorage–independent cell proliferation," *EMBO 14*:1187–1197 (1995).

Chen, J.–Y., et al., "Two distinct actions of retinoid–receptor ligands," *Nature 382*:819–822 (1996).

Fanjul, A., "The Ying–yang of RAR and AP–1: cancer treatment without overt toxicity," *Human and Exp. Toxic. 14*:226–230 (1995).

Fanjul, A., "Antiproliferative effects of a new class of retinoids with selective anti–AP–1 activity in various cancer lines," *Proc. Am. Assoc. Cancer Res. 36*:509, Abstract No. 3030 (1995).

Guérin, E., et al., "Stromelysin–3 Induction and Interstitial Collagenase Repression by Retinoic Acid," *J. Biol. Chem. 272*:11088–11095 (Apr. 1997).

Nagpal, S., et al. "Separation of Transactivation and AP1 Antagonism Functions of Retinoic Acid Receptor α," *J. Biol. Chem. 270*:923–927 (1995).

* cited by examiner

METHODS AND COMPOSITIONS FOR USE IN MODULATING EXPRESSION OF MATRIX METALLOPROTEINASE GENES

CROSS REFERENCE TO RELATED APPLICATION

This application claims the benefit of U.S. Provisional Application No. 60/044,258, filed Apr. 24, 1997, the disclosure of which is incorporated herein by reference in its entirety.

BACKGROUND OF THE INVENTION

1. Field of the Invention

The present invention relates to the fields of mammalian gene expression, retinoid receptor biology and mammalian disease therapeutics. Specifically, the present invention relates to methods for identifying compositions useful in differentially modulating the expression of two or more mammalian genes, particularly matrix metalloproteinase (MMP) genes. In addition, the invention relates to methods of treating a mammal (such as a human) suffering from or predisposed to a physical disorder, using pharmaceutical compositions comprising the compositions identified by the above-described methods. The methods and compositions of the present invention are useful in treating a variety of physical disorders in mammals including cancers (particularly carcinomas), inflammatory disorders, fibrotic disorders, ocular disorders and osteoporosis.

2. Related Art

Matrix Metalloproteinases

The matrix metalloproteinase (MMP) family consists of extracellular proteinase with amino acid sequence homologies and similarities in protein domain organization, which have been implicated in a variety of tissue remodeling processes (Hembry, R. M., et al., *Am. J. Pathol.* 143(2):628–642(1993); Murphy, G.,*Acta Orthop. Scand.* 66 (Suppl. 266):55–60 (1995)). One member of the MMP family is stromelysin-3, the expression of which has been associated with cutaneous wound healing (Okada, A., et al., *Gene*185:187–193 (1997)), mammary gland involution (Lefebvre, O., et al., *J. Cell Biol.* 119:997–1002 (1992)), cycling endometrium (Rodgers, W. H., et al.,*J. Clin. Invest.* 94:946–953 (1994)), embryonic development (Lefebvre, O., et al., *Development*121:947–955 (1995)) and metamorphosis (Patterson, D., et al, *Dev. Biol.* 167:252–262 (1995)), where its expression was predominantly found in cells of mesodermal origin. In human carcinomas, stromelysin-3 was the first MMP identified as being expressed by stromal cells (Basset, P., et al, *Nature*348:699–704 (1990); Rouyer, N., et al., *Metastasis*14:269–275 (1994)). Although human stromelysin-3 appears to be unable to degrade any major component of the extracellular matrix (Pei, D., et al.,*J. Biol. Chem.* 269:25849–25855 (1994); Noël, A., et al, *J. Biol. Chem* 270:22866–22872 (1995)) and exhibits unusual activation properties (Pei, D., and Weiss, S. J., *Nature*375:244–247 (1995); Santavicca, M., et al.,*Biochem. J.* 315:953–958 (1996)), its role in cancer progression is supported by high expression levels which are predictive of a poor clinical outcome (Engel, G., et al., *Int. J. Cancer* 58:830–835 (1994); Chenard, M.-P., et al., *Int. J. Cancer* 69(6):448–451 (1996)). Furthermore, stromelysin-3 has been shown to facilitate the tumor "take" of cancer cells in nude mice (Noël, A., et al., *J. Clin. Invest.* 97:1924–1930 (1996)).

Following the identification of stromelysin-3, a number of other MMPs were found to be expressed by stromal cells of human carcinomas (MacDougall, J. R., and Matrisian, L. M., *Canc. Metast. Rev.* 14:351–362 (1996)). Together, these results indicate that the production of MMPs by stromal cells represents a significant contribution to the overall proteolytic activities in malignant tumors (MacDougall, J. R., and Matrisian, L. M., *Cancer Metastasis Rev.* 14:351–362 (1996); Stetler-Stevenson, W. G., et al., *Semin. Cancer Biol.* 7:147–154 (1996), and references cited therein). Despite the observation that most stromal MMPs are expressed by fibroblastic cells, no regulatory sequence that could account for this cell-specific expression pattern has yet been identified in the promoter of the corresponding genes.

Retinoids

A number of studies have demonstrated that retinoids (vitamin A derivatives) are essential for normal growth, vision, tissue homeostasis, reproduction and overall survival (for reviews and references, See Sporn et al., *The Retinoids*, Vols. 1 and 2, Sporn et al., eds., Academic Press, Orlando, Fla. (1984)). For example, retinoids have been shown to be vital to the maintenance of skin homeostasis and barrier function in mammals (Fisher, G. J., and Voorhees, J. J., *FASEB J.* 10:1002–1013 (1996)). Retinoids are also apparently crucial during embryogenesis, since offspring of dams with vitamin A deficiency (VAD) exhibit a number of developmental defects (Wilson, J. G., et al., *Am. J. Anat.* 92:189–217 (1953); Morriss-Kay, G. M., and Sokolova, N., *FASEB J.* 10:961–968 (1996)). With the exceptions of those on vision (Wald, G., et al., *Science* 162:230–239 (1968)) and spermatogenesis in mammals (van Pelt, H. M. M., and De Rooij, D. G., *Endocrinology* 128:697–704 (1991)), most of the effects generated by VAD in animals and their fetuses can be prevented and/or reversed by retinoic acid (RA) administration (Wilson, J. G., et al. *Am. J. Anat.* 92:189–217 (1953); Thompson et al., *Proc. Royal Soc.* 159:510–535 (1964); Morriss-Kay, G. M., and Sokolova, N., *FASEB J.* 10:961–968 (1996)). The dramatic teratogenic effects of maternal RA administration on mammalian embryos (Shenefelt, R. E., *Teratology* 5, 103–108 (1972), Kessel, M., *Development* 115:487–501 (1992); Creech Kraft, J., In *Retinoids in Normal Development and Teralogeniesis*, G. M. Morriss-Kay, ed., Oxford University Press, Oxford, UK, pp. 267–280 (1992)), and the marked effects of topical administration of retinoids on embryonic development of vertebrates and limb regeneration in amphibians (Mohanty-Hejmadi, et al., *Nature* 355:352–353 (1992); Tabin, C. J., *Cell* 66:199–217 (1991)), have contributed to the notion that RA may have critical roles in morphogenesis and organogenesis.

Retinoid Receptors

Except for those involved in visual perception (Wald, G. et al., *Science* 162:230–239 (1968)), the molecular mechanisms underlying the highly diverse effects of retinoids have until recently remained obscure. The discovery of nuclear receptors for RA (Petkovich et al., *Nature* 330:444–450 (1987); Giguere et al., *Nature* 330:624–629 (1987)) has greatly advanced the understanding of how the retinoids may exert their pleiotropic effects (Leid et al., *TIBS* 17:427–433 (1992); Linney, E., *Current Topics in Dev. Biol.* 27:309–350 (1992)). Since this discovery it has become apparent that the genetic activities of the RA signal are mediated through two families of receptors—the RAR family and the RXR family—which belong to the superfamily of ligand-inducible transcriptional regulatory factors that include steroid/thyroid hormone and vitamin D3 receptors (for reviews see Leid et al., *TIBS* 17:427–433 (1992); Chambon, P., *Semin. Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

RAR Receptors

Receptors belonging to the RAR family (RAR$\alpha$, $\beta$ and $\gamma$ and their isoforms) ate activated by both all-trans- and 9-cis-RA (Leid et al., *TIBS* 17:427–433 (1992); Chambon, P., *Semin. Cell Biol.* 5:115–125 (1994); Dollé, P., et al., *Mech. Dev.* 45:91–104 (1994); Chambon, P., *FASEB J.* 10:940–954 (1996)). Within a given species, the DNA binding (C) and the ligand binding (E) domains of the three RAR types are highly similar, whereas the C-terminal domain F and the middle domain D exhibit no or little similarity. The amino acid sequences of the three RAR types are also notably different in their B regions, and their main isoforms ($\alpha$1 and $\alpha$2, $\beta$1 to $\beta$4, and $\gamma$1 and $\gamma$2) further differ in their N-terminal A regions (Leid et al., *TIBS* 17:427–433 (1992)). Amino acid sequence comparisons have revealed that the interspecies conservation of a given RAR type is greater than the similarity found between the three RAR types within a given species (Leid et al., *TIBS* 17:427–433 (1992)). This interspecies conservation is particularly striking in the N-terminal A regions of the various RAR$\alpha$, $\beta$ and $\gamma$ isoforms, whose A region amino acid sequences are quite divergent. Taken together with the distinct spatio-temporal expression patterns observed for the transcripts of each RAR and RXR type in the developing embryo and in various adult mouse tissues (Zelent, A., et al., *Nature* 339:714–717 (1989); Dollé, P., et al., *Nature* 342:702–705 (1989); Dollé et al., *Development* 110:1133–1151 (1990); Ruberte et al., *Development* 108:213–222 (1990); Ruberte et al., *Development* 111:45–60 (1991); Mangelsdorf et al., *Genes & Dev.* 6:329–344 (1992)), this interspecies conservation has suggested that each RAR type (and isoform) may perform unique functions. This hypothesis is further supported by the finding that the various RAR isoforms contain two transcriptional activation functions (AFs) located in the N-terminal A/B region (AF-1) and in the C-terminal E region (AF-2), which can synergistically, and to some extent differentially, activate various RA-responsive promoters (Leid et al., *TIBS* 17:427–433 (1992); Nagpal, S., et al., *Cell* 70:1007–1019 (1992); Nagpal, S., et al., *EMBO J.* 12:2349–2360 (1993)).

RXR Receptors

Unlike the RARs, members of the retinoid X receptor family (RXR$\alpha$, $\gamma$ and $\gamma$) are activated exclusively by 9-cis-RA (Chambon, P., *FASEB J.* 10:940–954 (1996); Chambon, P., *Semin. Cell Biol.* 5:115–125 (1994); Dollé, P., et al., *Mech. Dev.* 45:91–104 (1994); Linney, E., *Current Topics in Dev. Biol.* 27:309–350 (1992); Leid et al., *TIBS* 17:427–433 (1992); Kastner et al., in *Vitamin A in Health and Disease*, R. Blomhoff, ed., Marcel Dekker, New York (1993)). However, the RXRs characterized to date are similar to the RARs in that the different RXR types also differ markedly in their N-terminal A/B regions (Leid et al., *TIBS* 17:427–433 (1992); Leid et al., *Cell* 68:377–395 (1992); Mangelsdorf et al., *Genes and Dev.* 6:329–344 (1992)), and contain the same transcriptional activation functions in their N-terminal A/B region and C-terminal E region (Leid et al., *TIBS* 17:427–433 (1992); Nagpal, S., et al., *Cell* 70:1007–1019 (1992); Nagpal, S., et al., *EMBO J.* 12:2349–2360 (1993)).

RXR$\alpha$ and RXR$\beta$ have a widespread (possibly ubiquitous) expression pattern during mouse development and in the adult animal, being found in all fetal and adult tissues thus far examined (Mangelsdorf, D. J., et al., *Genes & Devel.* 6:329–344 (1992); Dollé, P., et al., *Mech. Devel.* 45:91–104 (1994); Nagata, T., et al., *Gene* 142:183–189 (1994)). RXR$\gamma$ transcripts, however, appear to have a more restricted distribution, being expressed in developing skeletal muscle in the embryo (where their expression persists throughout life), in the heart (after birth), in sensory epithelia of the visual and auditory systems, in specific structures of the central nervous system, and in tissues involved in thyroid hormone homeostasis, e.g., the thyroid gland and thyrotrope cells in the pituitary (Mangelsdorf, D. J., et al., *Gene & Devel* 6:329–344 (1992); Dollé, P., et al., *Mech. Devel.* 45:91–104 (1 994); Sugawara, A., et al., *Endocritnology* 136:1766–1774 (1995); Liu, Q., and Linney, E., *Mol. Endocrinol.* 7:651–658 (1993)).

It is currently unclear whether all the molecular properties of RXRs characterized in vitro are relevant for their physiological functions in vivo. In particular, it is unknown under what conditions these receptors act as 9-cis-RA-dependent tanscriptional regulators (Chambon, P., *Semin. Cell Biol.* 5:115–125 (1994)). The knock-outs of RXR$\alpha$ and RXR$\beta$ in the mouse have provided some insight into the physiological functions of these receptors. For example, the ocular and cardiac malformations observed in RXR$\alpha^{-/-}$ fetuses (Kastner, P., et al., *Cell* 78:987–1003 (1994); Sucov, H. M., et al., *Genes & Devel* 8:1007–1018 (1994)) are similar to those found in the fetal VAD syndrome, thus suggesting an important function of RXR$\alpha$ in the transduction of a retinoid signal during development The involvement of RXRs in retinoid signaling is further supported by studies of compound RXR$\alpha$/RAR mutants, which reveal defects that are either absent or less severe in the single mutants (Kastner, P., et al., *Cell* 78:987–1003 (1994); Kastner, P., et al., *Cell* 83:859–869 (1995)). Interestingly, however, knockout of RXR$\gamma$ in the mouse induces no overt deleterious effects, and RXR$\gamma^{-/-}$ homozygote which are also RXR$\alpha^{-/-}$ or RXR$\beta^{-/-}$ exhibit no additional abnormalities beyond those seen in RXR$\alpha^{-/-}$, RXR$\beta^{-/-}$ and fetal VAD syndrome fetuses (Krezel, W., et al., *Proc. Natl. Acad. Sci. USA* 93(17):9010–9014 (1996)), suggesting that RXR$\gamma$, despite its highly tissue-specific expression pattern in the developing embryo, is dispensable for embryonic development and postnatal life in the mouse. The observation that live-born RXR$\gamma^{-/-}$/RXR$\beta^{-/-}$/RXR$\alpha^{-/-}$ mutants can grow to reach adult age (Krezel et al., *Proc. Natl. Acad. Sci. USA* 93(17):9010–9014 (1996)) indicates that a single RXR$\alpha$ allele is sufficient to carry out all of the vital developmental and postnatal functions of the RXR family of receptors, particularly all of the developmental functions which depend on RARs and may require RXR partnership (Dollé, P., et al., *Mech. Dev.* 45:91–104 (1994); Kastner, P., et al., *Cell* 83:859–869 (1995)). Furthermore, the finding that RXR$\alpha^{-/-}$/RXR$\gamma^{-/-}$ double mutant embryos are not more affected than are single RXR$\alpha^{-/-}$ mutants (Krezel et al., *Proc. Natl. Acad. Sci. USA* 93(17):9010–9014 (1996)) clearly shows that RXR$\beta$ alone can also perform some of these functions. Therefore, i the fact that RXR$\alpha$ alone and, to a certain extent RXR$\beta$ alone, are sufficient for the completion of a number of developmental RXR functions, clearly indicates the existence of a large degree of functional redundancy amongst RXRs. In this respect, the RXR situation is different from that of RARs, since all of types of RAR double mutants displayed much broader sets of defects than single mutants (Rowe, A., et al., *Develop.* 111:771–778

(1991); Lohnes, D., et al., *Develop.* 120:2723–2748 (1994); Mendelsohn, C., *Develop.* 120:2749–2771 (1994)).

Retinoid Binding to RAR and RXR Receptors

The crystal structures of the ligand-binding domains (LBDs) of the RARs and RXRs have recently been elucidated (Bourget, W., et al., *Nature* 375:377–382 (1995); Renaud, J. P., et al., *Nature* 378:681–689 (1995); Wurtz, J. M., et al., *Nature Struct. Biol.* 3:87–94 (1996)). Among the various RAR types, substantial amino acid sequence identity is observed in these domains: comparison of the LBDs of RARα, RARβ and RARγ indicates that only three amino acid residues are variable in the ligand-binding pocket of these receptors. These residues apparently account for the fact that the various RAR types exhibit some selectivity in binding certain synthetic retinoids (Chen, J.-Y., et al., *EMBO J.* 14(6):1187–1197 (1995): Renaud, J. P., et al., *Nature* 378:68 1–689 (1995)), and consideration of these divergent residues can be used to design RAR type-specific synthetic retinoids which may be agonistic or antagonistic (Chambon, P., *FASEB J.* 10:940–954 (1996)). This design approach may be extendable generally to other nuclear receptors, such as thyroid receptor α (Wagner, R. L., et al., *Nature* 378:690–697 (1995)), the ligand-binding pockets of which may chemically and structurally resemble those of the RARs (Chambon, P., *FASEB J.* 10:940–954 (1996)). Conversely, molecular modeling of the ligand-binding pocket of the RXRs demonstrates that there are no overt differences in amino acid composition between RXRα, RXRβ and RXRγ (Bourguet, W., et al., *Nature* 375:377–382 (1995); Wurtz, J. M., et al., *Nature Struct. Biol.* 3:87–94 (1996)), suggesting that design of type-specific synthetic ligands for the RXRs may be more difficult than for the RARs (Chambon, P., *FASEB J.* 10:940–954 (1996)).

Retinoid Signaling Through RAR:RXR Heterodimers

Nuclear receptors (NRs) are members of a superfamily of ligand-inducible transcriptional regulatory factors that include receptors for steroid hormones, thyroid hormones, vitamin D3 and retinoids (Leid, M., et al., *Trends Biochem. Sci.* 17:427–433 (1992); Leid, M., et al., *Cell* 68:377–395 (1992); and Linney, E. *Curr. Top. Dev. Biol.*, 27:309–350 (1992)). NRs exhibit a modular structure which reflects the existence of several autonomous functional domains. Based on amino acid d sequence similarity between the chicken estrogen receptor, the human estrogen and glucocorticoid receptors, and the v-erb-A oncogene (Krust, A., et al., *EMBO J.* 5:891–897 (1986)), defined six regions—A, B, C, D, E and F—which display different degrees of evolutionary conservation amongst various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1 and AF-2 of steroid receptors exhibit differential transcriptional activation properties which appear to be both cell type and promoter context specific (Gronemeyer, H. *Annu. Rev. Genet.* 25:89–123 (1991)).

As described above, the all-trans (t-RA) and 9-cis (9C-RA) retinoic acid signals are transduced by two families of nuclear receptors, RAR α, β and γ (and their isoforms) are activated by both t-RA and 9C-RA, whereas RXR α, β and γ are exclusively activated by 9C-RA (Allenby, G. et al., *Proc. Natl. Acad. Sci. USA* 90:30–34 (1993)). The three RAR types differ in their B regions, and their main isoforms (α1 and α2, β1–4, and γ1 and γ2) have different N-terminal A regions (Leid, M. et al., *Trends Biochem. Sci.* 17.427–433 (1992)). Similarly, the RXR types differ in their A/B regions (Mangelsdorf, D. J. et al., *Genies Dev.* 6:329–344 (1992)).

The E-region of RARs and RXRs has also been shown to contain a dimerization interface (Yu, V. C. et al., *Curr. Opin. Biotechnol.* 3:597–602 (1992)). Most interestingly, it was demonstrated that RAR/RXR heterodimers bind much more efficiently in vitro than homodimers of either receptor to a number of RA response elements (RAREs) (Yu, V. C. et al., *Cell* 67:1251–1266 (1991); Berrodin, T. J. et al., *Mol. Endocrinol* 6:1468–1478 (1992); Bugge, T. H. et al., *EMBO J.* 11:1409–1418 (1992); Hall, R. K. et al., *Mol Cell. Biol.* 12: 5527–5535 (1992); Hallenbeck, P. L. et al., *Proc. Natl. Acad. Sci. USA* 89:5572–5576 (1992); Husmann, M. et al., *Biochem. Biophys. Res. Commun.* 187:1558–1564 (1992); Kliewer, S. A. et al., *Nature* 355:446–449 (1992); Leid, M. et al., *Cell* 68:377 395 (1992); Marks, M. S. et al., *EMBO J.* 11:1419–1435 (1992); Zhang, X. K. et al., *Nature* 355:441–446 (1992)). RAR and RXR heterodimers are also preferentially formed in solution in vitro (Yu, V. C. et al., *Cell* 67:1251–1266 (1991); Leid, M. et al., *Cell* 68:377–395 (1992); Marks, M. S. et al., *EMBO J.* 11:1419–1435 (1992)), although the addition of 9C-RA appears to enhance the formation of RXR homodimers in vitro (Lehman, J. M. et al., *Science* 258:1944–1946 (1992); Zhang, X. K. et al., *Nature* 358:587–591 (1992b)).

It has been shown that activation of RA-responsive promoters likely occurs through RAR:RXR heterodimers rather than through homodimers (Yu, V. C. et al., *Cell* 67:1251–1266 (1991); Leid et al., *Cell* 68:377–395 (1992b); Durand et al., *Cell* 71:73–85 (1992); Nagpal et al., *Cell* 70:1007–1019 (1992); Zhang, X. K, et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); Yu, V. C. et al., *Cur. Op. Biotech.* 3:597–602 (1992); Leid et al., *TIBS* 17:427–433 (1992); Laudet and Stehelin, *Curr. Biol.* 2:293–295 (1992); Green, S., *Nature* 361:590–591 (1993)). The RXR portion of these heterodimers has been proposed to be silent in retinoid-induced signaling (Kurokawa. R., et al., *Nature* 371:528–531 (1994); Forman, B. M., et al., *Cell* 81:541–550 (1995); Mangelsdorf, D. J., and Evans, R. M., *Cell* 83:835–850 (1995)), although conflicting results have been reported on this issue (Apfel, C. M., et al., *J. Biol. Chem.* 270(51):30765–30772 (1995); see Chambon, P., *FASEB J.* 10:940–954 (1996) for review). Although the results of these studies strongly suggest that RAR/RXR heterodimers are indeed functional units that transduce the RA signal in vivo, it is unclear whether all of the suggested heterodimeric combinations occur in vivo (Chambon, P., *Semin. Cell Biol.* 5:115–125 (1994)). Thus, the basis for the highly pleiotropic effect of retinoids may reside, at least in part, in the control of different subsets of retinoid-responsive promoters by cell-specifically expressed heterodimeric combinations of RAR:RXR types (and isoforms), whose activity may be in turn regulated by cell-specific levels of all-trans- and 9 cis-RA (Leid et al., *TIBS* 17:427–433 (1992)).

The RXR receptors may also be involved in RA-independent signaling. For example, the observation of aberrant lipid metabolism in the Sertoli cells of RXRβ$^{-/-}$ mutant animals suggests that functional interactions may also occur between RXRβ and the peroxisomal proliferator-activated receptor signaling pathway (WO 94/26100; Kastner, P., et al., *Genes & Devel.* 10:80–92 (1996)).

Retinoid Signaling and MMP Gene Expression

While MMP gene expression can be induced in human fibroblasts by agents such as phorbol ester (TPA) or growth factors (Basset, P., et al., *Nature* 348:699–704 (1990); Okada, A., et al., *Proc. Natl. Acad. Sci. USA* 92:2730–2734 (1995)), very little is known about the mechanisms regulating this expression. The stromelysin-3 gene has recently been isolated and characterized (Anglard, P., et al., *J Biol. Chem.* 270:20337–20344 (1995)), and the proximal promoter of this gene shown to differ from those of other MMPS by the absence of a consensus AP1 (c-jun/c-fos) binding site and the presence of a retinoic acid responsive element (RARE) of the DR1 type (DR1-RARE). This DR1-RARE can be transactivated by retinoid receptors (RARs/RXRs) in a ligand-dependent manner in transfected COS-1 cells. In contrast, AP1 binding sites were found to play a crucial role in controlling both the activation of other MMP gene promoters in response to growth factors and cytokines (McDonnell, S. E., et al., *Mol. Cell. Biol.* 10:42:34–4293 (1990); Lafyatis, R., et al., *Mol. Endocrinol.* 4:973–980 (1990)), and their inhibition by retinoic acid (RA) (Lafyatis, R., et al., *Mol. Endocrinol.* 4:973–980 (1990); Nicholson, R. C., et al., *EMBO J.* 9:4443–4454 (1990); Fanjul, A., et al., *Nature* 372:107–111 (1994)). Gene transcription studies have shown that while RARs and RXRs can induce transcriptional activation through specific DNA binding sites, they can also interact indirectly with AP1 through transcriptional mediators, in order to repress gene transcription (Yang-Yen, H. F., et al., *New. Biol.* 3:1206–1219 (1991); Pfahl, M., *Endocr. Rev.* 14:651–658 (1993); Chen, J.-Y., et al., *EMBO J.* 14:1187–1197 (1995)). In agreement with these findings, inhibition of baseline and TPA-induced RNA expression by RA has been reported for interstitial collagenase (Lafyatis, R., et al., *Mol. Endocrinol.* 4:973–980 (1990)) and stromelysin-1 (Nicholson, R. C., et al., *EMBO J.* 9:4443–4154 (1990)). However, many retinoids which inhibit the expression of interstitial collagenase and other AP1-containing MMP genes simultaneously activate stromelysin-3 (Anglard, P., et al., *J. Biol. Chem.* 270(35):20337–20344 (1995)). Thus, identification of potential therapeutic compounds which inhibit interstitial collagenase (and other AP1-binding site-containing genes) while not inducing, or only moderately inducing, stromelysin-3 (and other RARE-containing genes) has proven to be difficult.

Therapeutic Uses of Retinoids

As retinoic acid is known to regulate the proliferative and differentiative capacities of several mammalian cell types (Gudas, L. J., et al., *In The Retinoids*, 2nd ed., Sporn, M. B., et al., eds., New York: Raven Press, pp. 443–520 (1994)), retinoids are used in a variety of chemopreventive and chemotherapeutic settings. The prevention of oral, skin and head and neck cancers in patients at risk for these tumors has been reported (Hong, W. K. et al., *N. Engl. J. Med.* 315:1501–1505 (1986); Hong, W. K. et al., *N. Engl. J. Med.* 323:795–801 (1990); Kraemer, K. H. et al., *N. Engl. J. Med.* 318:1633–1637 (1988); Bollag, W. et al., *Ann. Oncol.* 3:513–526 (1992); Chiesa, F. et al., *Eur. J. Cancer B. Oral Oncol.* 28:97–102 (1992); Costa, A. et al., Cancer Res. 54:Suppl. 7, 2032–2037 (1994)). Retinoids have also been used to treat squamous cell carcinoma of the cervix and the skin (Verma, A. K., *Cancer Res.* 47:5097–5101 (1987); Lippman S. M. et al., *J. Natl Cancer Inst.* 84:235–241 (1992); Lippman S. M. et al., *J. Natl Cancer Inst.* 84:241–245 (1992)) and Kaposi's sarcoma (Bonhomme, L. et al., *Ann. Oncol.* 2:234–235 (1991)), and have found significant use in the therapy of acute promyelocytic leukemia (Huang, M. E. et al., *Blood* 72:567–572 (1988); Castaigne, S. et al., *Blood* 76:1704–1709 (1990); Chomienne, C. et al., *Blood* 76:1710–1717 (1990); Chomienne, C. et al., *J. Clin. Invest.* 88:2150–2154 (1991); Chen Z. et al., *Leukenia* 5:288–292 (1991); Lo Coco, F. et al., *Blood* 77:1(,57–1659 (1991); Warrell, R. P., et al., *N. Engl. J. Med.* 324:1385–1393 (1991 ); Chomienne, C., et al., *FASEB J.* 10:1025–1030 (1996)).

Despite extensive knowledge of RA action at the molecular level and the use of retinoids in treating a variety of physical disorders, however, only a few RA target genes have been identified. In the present invention, additional such genes are identified, and therapeutic methods and compositions acting through mechanisms that regulate the expression of these genes are provided.

BRIEF SUMMARY OF THE INVENTION

By the invention, methods are provided for screening one or more compositions to select a composition capable of differentially modulating the expression of a first and a second mammalian genes, wherein the first mammalian gene comprises at least one AP1-binding site and the second mammalian gene comprises it least one RARE. A preferred such method of the invention comprises:

(a) obtaining a first and a second mammalian cells comprising the first gene and the second gene;

(b) contacting the first mammalian cell, but not the second mammalian cell, with the compositions to be assayed;

(c) measuring the levels of expression of said first and second genes in said first and second mammalian cells;

(d) comparing the levels of expression of said first and second genes in said first mammalian cell to the levels of expression of said first and second genes in said second mammalian cell; and (e) selecting a composition wherein the level of expression of said first gene in said first mammalian cell is at least about 50% lower than the level of expression of said first gene in said second mammalian cell, and wherein the level of expression of said second gene in said first mammalian cell is no greater than about three-fold higher than the level of expression of said second gene in said second mammalian cell. In particularly preferred methods of the invention, the first and second genes are matrix metalloproteinase genes; most preferably, the first gene is an interstitial collagenase gene and the second gene is a stromelysin-3 gene. According to the invention, the measuring step (c) of the present methods preferably is accomplished by a method selected from the group consisting of northern blotting, western blotting and a reporter cell assay.

According to the invention, any composition capable of differentially modulating the expression of the first and second genes may be identified. Preferably, the invention is used to select compositions in step (e) of the above-described methods that comprise at least one RXR agonist or at least one RXR antagonist, and preferably at least one pan-RXR agonist which is most preferably BMS649. The compositions selected according to the methods of the invention may further comprise at least one RAR agonist or RAR antagonist, preferably at least one RARα agonist which is most preferably BMS753.

The invention also relates to methods of treating a mammal suffering from or predisposed to a physical disorder, comprising administering to the mammal an effective amount of a pharmaceutical composition comprising at least one compositor (and a pharmaceutically acceptable carrier therefor) capable of differentially modulating the expression of a first and a second mammalian genes, wherein the first mammalian gene comprises at least one AP1-binding site and the second mammalian gene comprises at least one RARE. The compositions which are contained in the pharmaceutical compositions used in these methods of treatment ate preferably selected from one or more compositions to be assayed according to the methods described above. The methods of the invention are useful in treating a variety of physical disorders in a mammal, particularly a human including a carcinoma, arthritis, osteoporosis, multiple sclerosis, atherosclerosis, corneal ulceration and diabetic retinopathy. Preferably used in the present methods are pharmaceutical compositions comprising at least one RXR agonist (which is more preferably a pan-RXR agonist and most preferably BMS649) or at least one RXR antagonist, and optionally further comprising at least one RAR agonist (which is more preferably a RARα agonist and most preferably BMS753) or at least one RAR antagonist.

Other preferred embodiments of the present invention will be apparent to one of ordinary skill in light of the following drawings and description of the invention, and of the claims.

BRIEF DESCRIPTION OF THE DRAWINGS

FIG. 1A: cells treated with 1 μM 9C-RA for 1–4 days. FIG. 1B: cells treated with 9C-RA concentrations ranging from 0.1 nM to 1 μM for 3.5 days.

FIGS. 8A and 8C) or RARγ- (CD666; FIGS. 8B and 8D) specific synthetic retinoids and/or with a pan-RXR(α,β,γ)-selective agonist (BM649).

DETAILED DESCRIPTION OF THE INVENTION

Overview

Figure 1:
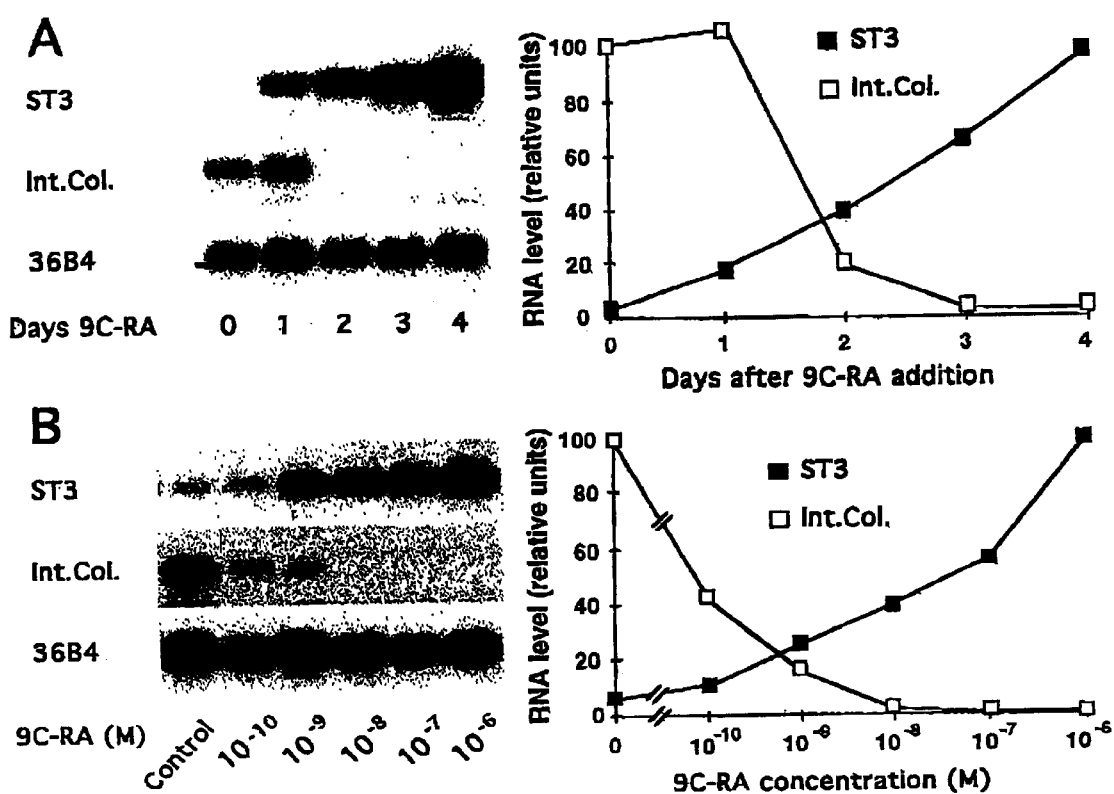
FIGS. 1A–1B are autoradiographs (and corresponding histograms) of northern blots demonstrating time course and dose response of stromelysin-3 and interstitial collagenase RNA expression in HFL1 fibroblasts treated with 9-cis-retinoic acid (9C-RA).

The present invention provides methods for the screening of one or more compositions to select a composition capable of differentially modulating the expression of a first and a second mammalian genes. By "differentially modulating the expression of a first and second mammalian genes" is meant that the composition affects (induces, inhibits or has no activity on) the expression of the first mammalian gene to a different extent than the composition affects the expression of the second mammalian gene. For example, a compound is said to "differentially modulate" the expression of a first and second mammalian genes in a mammalian cell if it inhibits the expression of the first mammalian gene by at least 50% (when compared to the expression of that same gene in a control cell not treated with the compound) while inducing the expression of the second mammalian gene by three-fold or less (again, compared to the level of expression of the second gene in a control cell). Of course, a compound is said to "differentially modulate" the expression of these genes if it induces the expression of both genes (at different levels), inhibits the expression of both genes (at different levels), induces one and inhibits the other, induces one and has no effect on the other, or inhibits one and has no effect on the other.

According to the invention, the first mammalian gene preferably comprises at least one AP1-binding site and is more preferably a matrix metalloproteinase gene and most preferably an interstitial collagenase gene, and the second mammalian gene comprises at least one RARE and is most preferably a stromelysin-3 gene. In general, the methods of the invention comprise obtaining cells comprising the first and second genes, contacting the cells with one or more of the compositions to be assayed, determining the levels of expression of the genes in the cells contacted with the compositions to be assayed, comparing the levels of expression of the genes in these cells to those in control cells not contacted with the compositions, and selecting a composition demonstrating the ability to inhibit the expression of a first gene by at least 50% while only inducing the expression of a second gene by less than about three-fold.

According to the invention, any composition capable of differentially modulating the expression of the first and second genes may be identified. Preferably, the invention is used to select compositions that comprise at least one RXR agonist or at least one RXR antagonist, and preferably at least one pan-RXR agonist which is most preferably BMS649. The compositions selected according to the methods of the invention may further comprise at least one RAR agonist or RAR antagonist, preferably at least one RARα agonist which is most preferably BMS753.

The invention also relates to methods of treating a mammal suffering from or predisposed to a physical disorder, comprising administering to the mammal an effective amount of a pharmaceutical composition comprising at least one composition (and a pharmaceutically acceptable carrier therefor) capable of differentially modulating the expression of a first and a second mammalian genes, wherein the first mammalian gene comprises at least one AP1-binding site and the second mammalian gene comprises at least one RARE. The compositions which are contained in the pharmaceutical compositions used in these methods of treatment are preferably selected from one or more compositions to be assayed according to the methods described above. The methods of the invention are useful in treating a variety of physical disorders in a mammal, particularly a human, including a carcinoma, arthritis, osteoporosis, multiple sclerosis, atherosclerosis, corneal ulceration and diabetic retinopathy. Preferably used in the present methods are pharmaceutical compositions comprising at least one RXR agonist (which is more preferably a pan-RxR agonist and most preferably BMS649) or at least one RXR antagonist, and optionally further comprising at least one RAR agonist (which is more preferably a RARα agonist and most preferably BMS753) or at least one RAR antagonist.

Screening of Compositions

In a first preferred embodiment, the invention provides methods of identifying or selecting compositions or compounds capable of differentially modulating the expression of two or more mammalian genes. According to the invention, compositions capable of differentially modulating the expression of the two or more mammalian genes are selected from among a plurality of compositions to be assayed for this capability, preferably by a cell-based assay. In general, compositions are screened for this capability according to a method comprising the steps of:

(a) obtaining a first and a second mammalian cells comprising the first gene and the second gene;

(b) contacting the first mammalian cell, but not the second mammalian cell, with the compositions to be assayed, (c) measuring the levels of expression of said first and second genes in said first and second mammalian cells;

(d) comparing the levels of expression of said first and second genes in said first mammalian cell to the levels of expression of said first and second genes in said second mammalian cell; and (e) selecting a composition wherein the level of expression of said first gene in said first mammalian cell is at least about 50% lower than the level of expression of said first gene in said second mammalian cell, and wherein the level of expression of said second gene in said first mammalian cell is no greater than about three-fold higher than the level of expression of said second gene in said second mammalian cell.

Screening Methods

The first and second mammalian cells used in the present selection methods may be normal cells, diseased cells, transformed cells or established cell lines, and may be epithelial cells, stromal cells (e.g., fibroblasts), stem cells, neuronal cells, osteocytes, chondrocytes, cancer cells (e.g., carcinoma, sarcoma or leukemia cells) and the like. According to the invention, the first and second mammalian cells are of the same type and undergo the same incubation conditions, except that the first mammalian cell is contacted with one or more of the compositions to be assayed for its ability to differentially modulate the expression of the two or more genes in the cell, while the second mammalian cell is incubated in parallel with the first cell but in the absence of the one or more compositions to be assayed. Thus, the second mammalian cell serves as a "control" cell to indicate the levels of expression of the two or more genes typically seen in that particular cell type in the absence of the compositions to be assayed, and provides a reference for determining the effects of the compositions on gene expression. As an alternative to using normal, diseased or established cells, transfected cell lines may be constructed and used in the methods of the invention. For example, in Chen et al., *EMBO J*. 14(6):1187–1197 (1995), three 'reporter' cell lines have been used to characterize a number of RARα-, RARβ-, or RARγ-specific dissociating synthetic retinoids that selectively induce the AF-2 activation function present in the ligand-binding domain (LBD) of RARβ (βAF-2). These cell lines stably express chimeric proteins containing the DNA binding domain of the yeast transactivator GAL4 fused to the EF regions (which contain that LBD and the AF-2 activation function) of RARα (GAL-RARα), RARβ (GAL-RARβ) or RARγ (GAL-RARγ), and a luciferase reporter gene driven by a pentamer of the GAL4 recognition sequence ("17 m") in front of the β-globin promoter (17 m) 5-GAL-Luc). In these cell lines, the RAR ligands thus induce luciferase activity that can be measured in the intact cells using a single-photon-counting camera. This reporter system is insensitive to endogenous receptors which cannot recognize the GAL4 binding site. Using analogous screening assays, these synthetic retinoids, like RA, have been reported to inhibit the anchorage-independent growth of oncogene-transformed 3T3 cells, while the promoter of the human interleukin-6 (IL-6) gene, whose product is involved in the regulation of hematopoiesis, immune responses and inflammation (Kishimoto, T. et al., *Science* 258:593–597 (1992)), has been shown to be induced by RA but not by the synthetic dissociating retinoids which repressed its activity. In a similar manner, RXR agonists have been identified using cell lines that express a RXR receptor linked to a TREpal-tk reporter gene which is activated by both RAR-RXR heterodimers and RXR homodimers (Lehmann, J. M., et al., *Science* 258:1944–1946 (1992)). Thus, reporter cell lines that are easily constructed, by methods routine to one of ordinary skill, may be used to distinguish not only the specific RAR or RXR types to which a candidate ligand will bind, but also whether that binding induces an activating or inhibiting (i.e., agonistic or antagonistic) effect. Although the above-referenced reporter cell lines comprised the luciferase or thymidine kinase genes as reporters, other reporters such as Neo, CAT, β-galactosidase or Green Fluorescent Protein are well known in the art and may be used in a similar fashion to carry our the present invention. For example, the use of CAT reporters to measure retinoic acid inhibition of stromelysin-1 gene expression has been reported (Nicholson, R. C., et al., *EMBO J*. 9(13):4443–4454 (1990)), and CAT reporters have been used in the methods of the present invention to examine RAR and RXR modulation of MMP gene expression, particularly of stromelysin-3 gene expression, as shown below in Example 4. Other references disclosing reporter plasmids containing a reporter gene and expression vectors encoding a LBD of a nuclear receptor include Meyer et al., *Cell* 57:433–442 (1989); Meyer et al., *EMBO J*. 9(12):3923–3932 (1990); Tasset et al., *Cell* 62:1177–1187 (1990); Gronemeyei, H., and Laudet, V., *Protein Profile* 2:1173–1308 (1995); Webster et al., *Cell* 54:199–207 (1988); Strähle et al., *EMBO J*. 7:3389–3395 (1988); Seipel et al., *EMBO J*. 11:4961–4968 (1992); and Nagpal et al., *EMBO J*. 12:2349–2360 (1993).

Other routine assays have been used to screen compounds for their agonistic properties on functions of other nuclear receptors, such as steroid receptors. For example, a transient expression/gel retardation system has been used to study the effects of the synthetic steroids RU486 and R5020 on glucocorticoid and progesterone receptor function (Meyer, M-E., et al., *EMBO J*. 9(12): 3923–3932 (1990)). Similar assays have been used to show that tamoxifen competitively inhibits estradiol-induced ERAP160 binding to the estrogen receptor, suggesting a mechanism for its growth-inhibitory effects in breast cancer (Halachimi, S., et al., *Science* 264:1455–1458 (1994)). Since the RAR and RKR receptors are apparently structurally similar to other nuclear receptors such as the steroid receptors (as reviewed in Chambon, P., *FASEB J*. 10:940–954 (1996)), routine assays of this type may be useful in assessing compounds for their abilities to modulate gene expression through RARs or RXRs.

As an alternative routine method, the effect of a candidate compound or compositor on the binding of the ligand-dependent AF-2 modulator TIF1 to a RAR or RXR LBD can be studied using glutathione-S-transferase (GST) interaction assays by tagging the LBDs with GST as described in detail in Le Douarin et al., *EMBO J*. 14:2020–2033 (1995).

In another screening assay, transgenic mice and cell lines that are altered in their expression of one or more RAR or RXR receptors may be made as described previously (Krezel, W., et al., *Proc. Natl. Acad. Sci. USA* 93(17):9010–9014 (1996)) and may be used to identify agonists of specific members of the RAR/RXR class of receptors using methods described previously (WO 94/26100). In such an assay, the agent which is to be tested will be incubated with one or more of the transgenic cell lines or mice or tissues derived therefrom. The level of binding of the agent is then determined, or the effect the agent has on development or gene expression is monitored, by techniques that are routine to those of ordinary skill. As used herein, the term "incubate" is defined as contacting the compound or agent under investigation with the appropriate cell or tissue, or administering the agent or compound to the appropriate mouse, via any one of the well-known routes of administration including enteral, intravenous, subcutaneous, and intramuscular.

Other assays, such as those described in detail below in the Examples, may also be used to predict the modulatory effects of RAR and RXR ligands on mammalian gene expression by determining the agonistic effects of these ligands on other targets. For example, certain agonistic retinoids will induce the association of endogenous PML/PML-RARα fusion protein with nuclear bodies in cells from APL patients (Dyck, J. A., et al., *Cell* 76:333–343 (1994); Weis, K., et al., *Cell* 76:345–356 (1994); Koken, M. H. M., et al., *EMBO J*. 13(5):1073–1083 (1994)) or in related established cell lines such as NB4 (Lanotte, M., et al., *Blood* 77(5):1080–1086 (1991)). These effects of RAR or RXR agonists or antagonists may be determined, for example, by various immunological techniques such as immunofluorescent or immunoelectron microscopy, using antibodies specific for PML, RAR and/or PML-RARα fusion proteins. RAR or RXR agonists may also be identified by their abilities to induce the in vitro differentiation (maturation) of certain established cell lines such as HL-60 myeloblastic leukemia cells (Nagy, L., et al., *Mol. Cell. Biol*. 15(7):3540–3551 (1995)), NB4 promyelocytic cells (Lanotte, M., et al., *Blood* 77(5):1080–1086 (1991), P19 or F9 embryonic carcinoma cells (Roy, B., et al., *Mol. Cell Biol*. 15(12):6481–6487 (1995); Horn, V., et al., *FASEB J*. 10:1071–1077 (1996)), or ras-transformed 3T3 cells (Chen et al., *EMBO J*. 14(6):1187–1197 (1995)). Ligand-induced differentiation in these and other cell lines may be determined by assaying ligand-treated or -untreated cells for the expression of a variety of well-known markers of differentiation as generally described in the above references.

Similarly, the candidate compounds may be screened by measuring their abilities to induce apoptosis (programmed cell death) in, for example, HL-60 cells (Nagy, L., et al., *Mol. Cell. Biol*. 15(7):3540–3551 (1995)) or P19 cells (Horn, V., et al., *FASEB J*. 10:1071–1077 (1996)), or in other primary cells or established cell lines. Apoptosis is typically assessed by measurement of ligand-induced DNA fragmentati on, which is accomplished by methods such as gel electrophoresis (appearance of smaller molecular weight bands), microscopy (changes in plasma membrane morphology such as formation of surface protruberances ("blebbing") or in nuclear morphology such as pycnosis or fragmentation) or expression of the putative apaptosis suppressive protein BCL-2 (decreased in apoptotic cells); for general methods and discussions of these assays as they pertain to RAR and RXR biology: see Nagy, L , et al., *Mol. Cell. Biol*. 15(7):3540–3551 (1995); Horn, V., et al., *FASEB J*. 10:1071–1077 (1996)). Other methods for assaying ligand-induced apoptosis in primary cells and established cell lines, such as flow cytometry or particle analysis (appearance of smaller particles with different light scatter and, or DNA content profiles), are well-known in the art (Telford, W. G., et al.,*J Immunol. Meth*. 172(1):1–16 (1994); Campana, D., et al., *Cytometry* 18(2):68–74 (1994); Sgonc, R., and Wick, G., *Int. Arch. Allergy Immunol*. 105(4):327–332 (1994); Fraker, P. J., et al., *Meth. Cell Biol*. 46:57–76 (1995); Sherwood, S. W., and Schimke, R. T., *Meth. Cell Biol*. 46:77–97 (1995); Carbonari, M., et al., *Cytometry* 22(3):161–167 (1995); Mastrangelo, A. J., and Betenbaugh, M. J., *Curr. Opin. Biotechnol*. 6(2):198–202 (1995)). Screening of agonists may also be accomplished by an assay known as "in vivo footprinting" (Mueller, P. R., and Wold, B., *Science* 246:780–786 (1989); Garrity, P. A., and Wold, B. J., *Proc. Natl. Acad. Sci. USA* 89:1021–1025 (1992)), which has proven useful for analysis of RA-induced transcription of RARβ2 (Dey, A., et al., *Mol. Cell. Biol*. 14(12):8191–8201 (1994)).

Finally, the effects of candidate compositions or compounds on mammalian gene expression, particularly on MMP gene expression, may be determined in cellular or animal models using assays that directly measure increases in MMP protein levels in extracellular fluid (e.g., culture media) or tissue samples by immunological or immunohistochemical techniques (see, e.g., Hembry, R. M., et al., *Am. J. Pathol*. 143(2):628–642 (1993)).

Other methods for determining the ability of a candidate ligand to modulate mammalian gene expression, particularly MMP gene expression, which are routine in the art, may also be used in carrying out the present invention. In performing such assays, one skilled in the art will be able to determine which RAR or RXR receptor type an agent binds to, what specific receptor(s) are utilized by a given compound, whether the agent is an agonist or an antagonist of the given receptor(s), and whether the compound or combination of compounds are capable of differentially modulating mammalian gene expression.

Genes

Preferably, the first and second mammalian genes to be modulated by the compounds identified or selected according to the methods of the invention are a first mammalian gene which preferably comprises at least one AP1-binding site, and a second mammalian gene which preferably comprises at least one retinoic acid response element (RARE).

Preferred AP1-binding site-containing genes according to the invention include matrix metalloproteinase (MMP) genes, growth factor response genes, cytokine response genes and the like. More preferable AP1-binding) site-containing genes according to the invention are MMP genes, including but not limited to those genes encoding interstitial collagenase, stromelysin-1, stromelysin-2, matrilysin and gelatinase B; most preferable is an interstitial collagenase gene. Preferred AP1-binding site-containing genes according to the invention include MWP genes, particularly a stromelysin-3 gene.

According to the invention, the first mammalian cell, but not the second mammalian cell, is contacted with the one or more compositions to be assayed. The levels cf expression of the first mammalian gene (preferably comprising one or more AP1-binding sites) and of the second mammalian gene (preferably comprising one or more RAREs) are then determined in the first and second cells according to one or more of the above-described assays. The level of expression of the first gene in the first cell is then compared to the level of expression of the first gene in the second (control) cell; this comparison is then repeated for the second gene in each cell. A compound or composition is then selected as differentially modulating the expression of the first and second genes if:

(a) the level of expression of the first gene in the first cell is at least about 50% lower, preferably at least about 55% lower, more preferably at least about 60%, 65%, 70%, 75%, 80%, 83%, 85%, 87%, 90%, 95% or 99% lower, than the level of expression of the first gene in the second (control) cell; and (b) the level of expression of the second gene in the first cell is no greater than about three-fold, more preferably no greater than about two-fold or about one-fold, higher than the level of expression of the second gene in the second (control) cell.

Thus, the invention provides a high-throughput screening assay for rapidly identifying compounds or compositions that are capable of differentially modulating the expression of two or more mammalian genes such as MMP genes, particularly wherein a first such gene comprises one or more AP1-binding sites (such as an interstitial collagenase gene) and a second such gene comprises one or more RAREs (such as a stromelysin-3 gene).

Selection and Synthesis of Candidate Compounds and Compositions

Thus, the methods of the invention may be used to select or identify one or more compounds or compositions that are capable of differentially modulating the expression of two or more genes. Compounds or compositions selected according to these methods can be, but are not limited to, peptides, carbohydrates, steroids and vitamin derivatives, which may each be natural or synthetic, and are preferably retinoids or retinoid derivatives that bind to one or more RARs or RXRs. The agents can be selected and screened at random, or can be rationally selected or rationally designed using protein modeling techniques. For random screening, agents such as peptides, carbohydrates, steroids or vitamin derivatives (e.g., derivatives of RA) are selected at random and are assayed, using direct or indirect methods that are routine in the art, for their ability to bind to a RAR or RXR receptor or a functional retinoid RAR:RXR receptor heterodimer. For example, candidate RAR agonists according to the present invention include synthetic retinoids such as Am580, Compound 1 and Compound 2 (the structures of which are disclosed in Ostrowski et al., *Proc. Natl. Acad. Sci. USA* 92:1812–1816 (1995), which is incorporated herein in its entirety), Am80 or CD666 (Roy et al., *Mol. Cell. Biol.* 15(12):6481–6487 (1995)), and BMS753 (Taneja, R., et al., *Proc. Natl. Acad. Sci. USA* 93:6197–6202 (1996)). Candidate RXR agonists according to the present invention include synthetic retinoids such as SR11237 (also known as BMS649, the structure of which is disclosed in Lehman, J. M., el al., *Science* 258:1944–1946 (1992), which is incorporated herein in its entirety). Other candidate RAR agonists and antagonists, and RXR agonists and antagonists., which may be used in the methods of the invention are described in U.S. application Ser. No. 60/024,772, filed Aug. 28, 1996, the disclosure of which is incorporated herein in its entirety.

Alternatively, agents may be rationally selected. As used herein, an agent is said to be "rationally selected" when the agent is chosen based on the physical structure of a known ligand of a RAR or RXR receptor or a functional heterodimeric RAR:RXR retinoid receptor. For example, assaying compounds possessing a retinoic acid-like structure would be considered a rational selection since retinoic acid-like compounds are known to bind to a variety of retinoid receptor heterodimers.

Since highly purified RAR and RXR proteins are now available, X-ray crystallography and NMR-imaging techniques, or techniques based on a computer model of the LBD of one or more RAR or RXR receptor types, can be used to identify the structure of the ligand binding site present on these proteins and, by extension, that which is specifically present on one or more RAR or RXR receptor types. For example, the crystal structure of the ligand binding domains of certain nuclear receptors have been described. In particular, the crystal structure of the RXR LBD is described in Bourguet et al., *Nature* 375:377–382 (1995), and the crystal structure of the RAR LBD is described in Renaud et al., *Nature* 378:681–689 (1995). Using information from the crystal structure of a RAR or RXR, computer programs are available that allow one to "rationally design" candidate agonists which would likely bind to the receptor ligand binding domains (Hodgson, *Biotechnology* 8:1245–1247 (1990); Hodgson, *Biotechnology* 9:609–613 (1991)). Suitable computer program packages for this purpose include WHAT IF (Vriend, G., *J. Mol. Graphics* 8:52–56 (1990)), and GRID (Goodford, *J. Med. Chem.* 28:849–857 (1985)). Using the predicted structure obtained via such computer modeling, candidate agonist compounds may be generated by methods of synthetic organic and inorganic chemistry that are known in the art.

Preferred compositions selected according to the invention are those comprising at least one RXR agonist or at least one RXR antagonist, and more preferably those compositions comprising at least one pan-RXR agonists. By "pan-RXR agonist" is meant an agent that binds to and activates a plurality of RXR isoforms, for example an agent that binds to and activates RXRα, RXRβ and RXRγ. In particular, the methods of the invention preferably are used to select those compositions comprising the pan-RXR agonists BMS649 (also known as SR11237, the structure of which is disclosed in Lehman, J. M., et al., *Science* 258:1944 1946 (1992)) or LG1069 (the structure and preparation of which are described in Boehm et al., *J. Med. Chem.* 37:2930–2941 (1994)).

The compositions selected according to the methods of the invention may further comprise at least one RAR agonist or at least one RAR antagonist. More preferably, the compositions selected according to the methods of the invention comprise at least one RARα agonist, at least one RARβ agonist or at least one RARγ agonist. In particular, the methods of the invention may be used to select compositions comprising Am80 (Roy et al., *Mol. Cell. Biol.* 15(12) :6481–6487 (1995)) or BMS753 (Taneja, R., et al., *Proc. Natl. Acad. Sci. USA* 93:6197–6202 (1996)), and most preferably BMS753 which has the following structure:

BMS753:

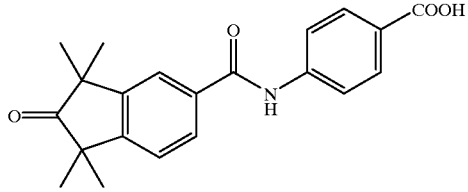

This compound may be prepared as follows:

Overview

Compound I (1,1,3,3-tetramethylindan-2-one), is known in the literature (Langhals. E., and Langhals, H., *Tet. Lett.* 31:859 (1990) and Bruson, H. A., et al., *J. Amer. Chem. Soc.* 80:3633 (1958)). I is acylated with ethyl oxalyl chloride/ auminum chloride to give keto-ester II, which is hydrolyzed using base to give to give keto acid III. III is oxidatively decarboxylated using aqueous hydrogen peroxide to give acid IV, which is activated by conversion to its acid chloride using thionyl chloride and their condensed with commercially available methylp-aminobenzoate to give amide-ester V. V is then cleaved using hydroxide base to give final product VI (BMS753).

Detailed Methods a.) Synthesis of Compound II—Ethyl 2(1',1',3'3'-tetranmethyl-2-keto-indan-5-yl)-2-oxoacetate To a stirring suspension of 16.8 gm $AlCl_3$ in 85 ml methylene chloride is added 5 ml ethyl oxalyl chloride. This mixture is stirred at room temperature for half an hour, then 2.9 gm of I is added and the mixture is stirred at room temperature for a further 2 hr, then poured over ~1 kg crushed ice. The layers are separated after the ice melts, the aqueous layer is washed with methylene chloride, and the combined organic layers are washed with saturated NaCl solution, dried over $MgSO_4$, filtered, and evaporated. The resulting oil is re-dissolved in ethyl acetate, back-extracted with $NaHCO_3$ solution, dried again, and evaporated to give 2.3 gm yellow/orange oil (II). Thin layer chromatography (10% ethyl acetate/hexane on silica gel) shows main compound $R_f$ 0.35.

Infrared spectrum (NaCl plates): 2969, 1746, 1686, 1184 $cm^{-1}$; NMR ($CDCl_3$): δ 7.95 (m, 2H), 7.41 (d, J=8.4, 1H), 4.48 (q, J=7, 2H), 1.44 (t, J=7, 3H), 1.38 (s, 6H), 1.37 (s, 6H).

b.) Synthesis of Compound III—2(1',1',3',3'-tetramethyl-2-keto-indan-5'-yl)-2-oxoacetic acid Compound II (2.3 gm) is dissolved in 200 ml methanol, and 50 ml 1 N NaOH is added. This mixture is stirred at room temperature for half an hour. The solvent is then evaporated, the residue dissolved in water, and the aqueous solution is washed with ethyl acetate. The aqueous phase is next acidified with concentrates HCl and the precipitated solid extracted into ethyl acetate. This organic phase is separated, washed with saturated NaCl solution, dried over $MgSO_4$, filtered, and evaporated to give 1.1 gm III as an orange oil which solidifies to a yellow solid. Thin layer chromatography (30% ethyl acetate/hexane +1% formic acid on silica gel) shows the main component at $R_f$ 0.2.

Infrared spectrum (KBr pellet): Broad absorption 3400–2500, 2971, 1751, 1726, 1686, 1611, 1167$cm^{-1}$. NMR ($CDCl_3$): δ 8.33 (d of d, J=8, J=1.74, 1H), 8.26 (d, J=1.68, 1H), 7.44 (d, J=8, 1H), 1.40 (s, 6H), 1.39 (s, 6H).

c.) Synthesis of Compound IV—1',1',3',3'-tetramethyl-2-keto-indan-5-yl-carboxylic acid To a solution of 1.1 gm III in 15 ml methanol is added 90 ml 1 N NaOH and 5 ml 30% $H_2O_2$, then the mixture is stirred at room temperature overnight. The solution is washed with 65 ml ethyl ether, then acidified with concentrated HCl, and the precipitated acid extracted into ethyl acetate, which is washed with saturated NaCl solution, dried with $MgSO_4$, filtered, and evaporated to give 1 gm white solid (IV). Thin layer chromatography (30% ethyl acetate/ hexane +1% formic acid on silica gel) shows the main component at $R_f$ 0.4.

NMR ($CDCl_3$): δ 8.09 (d of d, J=8, J=1.65, 1H), 8.04 (d, J=1.65, 1H), 7.39 (d, J=8, 1H), 1.40 (s, 6H), 1.39 (s, 6H).

d.) Synthesis of Compound V—Methyl 4(1',1',3',3'-tetramethyl-2'-keto-indan-5'-carboxamido)benzoate Compound IV (1.1 gm) is suspended in 25 m methylene chloride and 0.6 ml oxalyl chloride is added, followed by a few drops of DMF. The reaction mixture is stirred at room temperature for a few minutes after the reaction subsides, then the solvent is removed in vacuo, the residue is dissolved in 20 mL pyridine, 70 mg, methyl p-aminobenzoate is added and the final mixture stirred at room temperature for 16 hr. The pyridine is then removed in vacuo, and the residue is partitioned between water and ethyl acetate. The organic layer is extracted 6 times with 1 N HCl solution, then washed with $Na_2CO_3$ solution and saturated NaCl, dried over $MgSO_4$, filtered, evaporated, and the residue purified by column chromatography on silica gel in 25% ethyl acetate/hexane. The main component with $R_f$=0.3 is collected to give 715 mg of white solid (V).

Infrared spectrum (KBr pellet): 3318, 2967, 1750, 1725, 1640, 1560, 1281 $cm^{-1}$. NMR ($CDCl_3$): δ 8.08 (d, J=6.7, 2H), 7.94 (d, J=1, 1H), 7.80 (d of d, J=8, J=1, 1H), 7.75 (d, J=6.7, 2H), 7.4 (d, J=7.7, 1H), 3.93 (s, 3H), 1.40 (s, 6H), 1.38 (s, 6H). Mass spectrum: M/Z=365.

e.) Synthesis of Compound VI—4(1',1',3',3'-tetramethyl-2'-keto-indan-5'-carbox-amido) benzoic acid (BMS753)

Compound V (700 mg) is dissolved in 90 ml warm methanol, then 6 ml of 1 N NaOH is added and the resulting solution refluxed for 4 hours. The solvent is evaporated off, the residue is dissolved in water and the aqueous solution is washed with ether then acidified with concentrated HCl, the precipitated acid extracted into ethyl acetate, washed with saturated NaCl, dried over $MgSO_4$, filtered, evaporated, and the solid recrystallized from methanol/water. Yield 450 mg white needles, forming the final compound BMS753 (VI). M.p. 267–267.5° Thin layer chromatography (30% ethyl acetate/hexane +1% formic acid on silica gel) shows a single component of $R_f$ 0.25.

Infrared spectrum (KBr pellet): 3439, broad absorption 3500–2500, 2960, 1750, 1682, 1607, 1518 $cm^{-1}$; NMR ($CDCl_3$): δ 7.95 (m, 6H), 7.58 (d, J=8, 1H), 1.34 (s, 6H), 1.31 (s, 6H); Elemental analysis: Calculated C, 71.78; H, 6.02; N, 3.99; O, 18.21; %. Found C, 71.85; H, 6.05; N, 4.01, O, 18.09; (diff) %. Mass Spectrum: M/Z=351.

Other RAR and RXR agonists suitable for use in the present invention may be prepared by the above-cited methods and others routine to those of ordinary skill in the art.

Clinical Indications

Thus, methods for identifying compositions or compounds capable of differentially modulating the expression of two or more mammalian genes are provided by the present invention. The compounds or compositions identified according to these methods may then be used, in another preferred embodiment of the invention, in methods for the treatment of a variety of physical disorders in animals (particularly mammals including humans) that are predisposed to or suffering from a physical disorder that may be delayed, prevented, cured or otherwise treated by differentially modulating the expression of two or more genes in the mammal, preferably by differentially modulating the expression of two or more MMP genes and most preferably by differentially modulating the expression of an interstitial collagenase gene and a stromelysin-3 gene. As used herein, an animal that is "predisposed to" a physical disorder is defined as an animal that does not exhibit a plurality of overt physical symptoms of the disorder but that is genetically, physiologically or otherwise at risk for developing the disorder. The compositions identified by the methods of the invention, which preferably comprise at least one RXR agonist (more preferably a pan-RXR agonist and most preferably BMS649) or at least one RXR antagonist, and which may further comprise at least one RAR agonist (more preferably a RARα agonist and most preferably BMS753) or at least one RAR antagonist, may thus be used prophylactically as chemopreventive agents for such disorders.

According to the invention, a mammal (preferably a human) that is predisposed to or suffering from a physical disorder may be treated by administering to the animal an effective dose of a composition or compound selected according to the above-described methods of the invention, in combination with a pharmaceutically acceptable carrier or excipient therefor (as described Delow). Physical disorders treatable with the compositions and methods of the present invention include any physical disorder that may be delayed, prevented cured or otherwise treated by modulating MMP gene expression in an animal suffering from or predisposed to the physical disorder. Such physical disorders include, but are not limited to, a variety of carcinomas and other cancers, such as skin cancers (including melanomas and Kaposi's Sarcoma), oral cavity cancers, lung cancers, breast cancers, prostatic cancers, bladder cancers, liver cancers, pancreatic cancers, cervical cancers, ovarian cancers, head and neck cancers, colon cancers, germ cell cancers (including teratocarcinomas) and leukemias. Other physical disorders treatable by the methods of the present invention include inflammatory disorders such as rheumatoid arthritis, multiple sclerosis, systemic lupus erythematosis, pelvic inflammatory disease and Crohn's disease. The methods of the invention may also be used to treat an animal suffering from or predisposed to a fibrotic disorder or disease, including pulmonary fibrosis, cystic fibrosis, endomyocardial fibrosis, hepatic fibrosis (particularly hepatic cirrhosis), myelofibrosis, scleroderma and systemic sclerosis. Other physical disorders treatable by the methods of the invention include osteoporosis, atherosclerosis, and ocular disorders such as corneal ulceration and diabetic retinopathy. The methods of the present invention may also be used in the prevention of disease progression, such as in chemoprevention of the progression of a premalignant lesion to a malignant lesion, and to treat an animal suffering from, or predisposed to, other physical disorders that respond to treatment with compositions that differentially modulate gene expression, particularly those that differentially modulate MMP gene expression and most particularly those that inhibit interstitial collagenase gene expression by at least 50% while only moderately inducing (i.e., by three-fold or less) stromelysin-3 gene expression.

Formulation and Methods of Administration

As indicated above, compositions and compounds selected according to the methods of the invention, such as RAR- and RXR-selective ligands, are known to elicit a wide array of cellular responses, several of which have clinical applications in treating a patient. The term "patient" as used herein is defined as an animal, preferably a mammal, including a human. As used herein, "an effective amount of a RAR (or RXR) agonist" is defined as an amount effective to elicit a cellular response in cells which express a RAR (or RXR) receptor. Example clinical therapies which involve administering compositions comprising at least one RAR agonist and at least one RXR agonist to a patient are discussed in more detail below.

The therapeutic methods of the invention thus use pharmaceutical composition comprising a composition selected for its ability to differentially modulate the expression of two or more mammalian genes as described above, and a pharmaceutically acceptable carrier or excipient therefor, which may be administered orally, rectally, parenterally, intrasystemically, intravaginally, intraperitoneally, topically (as by powders, ointments, drops or transdermal patch), bucally, or as an oral or nasal spray. Preferred such compositions comprise at least one agonist (preferably a pan-RXR agonist and most preferably BMS649) or at least one RXR antagonist, and may optionally further comprise at least one PRR agonist (preferably a RARα agonist and most preferably BMS753) or at least one RAR antagonist. Importantly, by co-administering a RXR agonist and/or antagonist, and a RAR agonist and/or antagonist, clinical side effects can be reduced by using lower doses of both the RAR-binding compound and the RXR-binding compound. It will be understood that the RXR agonist or antagonist can be "co-administered" either before, after, or simultaneously with the RAR agonist or antagonist, depending on the exigencies of a particular therapeutic application. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions used in the methods of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene ,lycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions used in the methods of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drugs, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compounds are mixed with it least one item pharmaceutically acceptable excipient or carrier such as sodium nitrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms oftablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredients in finely divided form may be used in admixture with a larger-sized pharmaceutically acceptable inert carrier comprising particles having a size, for example, of up to 100 $\mu$m in diameter. Suitable inert carriers include sugars such as lactose. Desirably, at least 95% by weight of the particles of the active ingredient have an effective particle size in the range of 0.01 to 10 $\mu$m.

Alternatively, the pharmaceutical composition may be pressurized and contain a compressed gas, such as nitrogen or a liquefied gas propellant. The liquefied propellant medium and indeed the total composition is preferably such that the active ingredients do not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye. The RAR agonist(s) and RXR agonist(s) are delivered in a pharmaceutically acceptable ophthalmic vehicle, such that the compounds are maintained in contact with the ocular surface for a sufficient time period to allow the compounds to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the RXR agonist(s)/antagonist(s) and optionally the RAR agonist(s)/antagonist(s) with suitable non-irritating excipients or carriers such as cocoa butter, polyethylene glycol or a suppository wax which are solid at room temperature but liquid at body temperature and therefore melt in the rectum or vaginal cavity and release the drugs.

The pharmaceutical compositions used in the present therapeutic methods may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present pharmaceutical compositions in liposome form can contain, in addition to the RXR agonist(s)/anttagonist(s) and optionally the RAR agonist(s)/antagonist(s), stabilizers, preservatives, excipients, and the like. The preferred lipids are the phospholipids and the phosphatidyl cholines (lecithins), both natural and synthetic. Methods to form liposomes are known in the art (see, e.g., Prescott, E., *Meth. Cell Biol.* 14:33 (1976)).

Dosaging

By the invention, a RXR agonist or antagonist can be administered in vitro, ex vivo or in vivo to cells to enhance the cellular response to a RAR agonist or antagonist. One of ordinary skill will appreciate that effective amounts of a RXR agonist or antagonist and a RAR agonist or antagonist can be determined empirically and may be employed in pure form or, where such forms exist, in pharmaceutically acceptable salt, ester or prodrug form. The RXR agonist(s)/antagonist(s) and RAR agonist(s)/antagonist(s) may be administered to a patient in need thereof as pharmaceutical compositions in combination with one or more pharmaceutically acceptable excipients. It will be understood that, when administered to a human patient, the total daily usage of the compounds and compositions of the present invention will be decided by the attending physician within the scope of sound medical judgement. The specific therapeutically effective dose level for any particular patient will depend upon a variety of factors including the type and degree of the cellular response to be achieved; activity of the specific RXR agonist/antagonist and RAR agonist/antagonist employed; the specific composition employed; the age, body weight, general health, sex and diet of the patient; the time of administration, route of administration, and rate of excretion of the RXR agonist/antagonist and RAR agonist/antagonist; the duration of the treatment; drugs used in combination or coincidental with the specific RXR agonist/antagonist and RAR agonist/antagonist; and like factors well known in the medical arts. For example, it is well within the skill of the art to start doses of RXR agonists/antagonists and/or RAR agonists/antagonists at levels lower than those required to achieve the desired therapeutic effect and to gradually increase the dosages until the desired effect is achieved.

For example, satisfactory results are obtained by oral administration of a RXR agonist/antagonist and a RAR agonist/antagonist at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging may also be arranged in a patient-specific manner to provide a predetermined concentration of a RXR agonist/antagonist and/or RAR agonist/antagonist in the blood, as determined by techniques accepted and routine in the art (HPLC is preferred). Thus patient dosaging may be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein are obvious and may be made without departing from the scope of the invention or any embodiment thereof Having now described the present invention in detail, the same will be more clearly understood by reference to the following examples, which are included herewith for purposes of illustration only and are not intended to be limiting of the invention.

EXAMPLES

Materials and Methods

The following materials and methods were generally used in all Examples:
Cell Culture.

Human fibroblasts (HFL1, CCL 153) and rhabdomyosarcoma cells (RD, CCL 136) were obtained from the American Type Culture Collection (Manassas, Va.) and maintained in monolayer culture in Dulbecco's modified Eagle's medium with or without 5% calf serum. Retinoids (t-RA, 9C-RA, BM753, BM649, Am80, and CD666) were dissolved in ethanol and added at desired concentrations for the time periods indicated in the figures.
RNA Extraction and Northern Blot Analysis.

Cell cultures were washed with phosphate buffered saline (PBS), and RNA extraction was carried out by the guanidine isothiocyanate phenol/chloroform procedure (Chomczynski, P., & Sacchi, N., *Anal. Biochem.* 162:156–159 (1987)). Ten to 30 µg of total RNA was denatured at 65° C. for 5 min and electrophoresed on 1% agarose gel prior to be transferred onto a nylon membrane (Hybond-N; Amersham) as previously described (Reiter, R. E., et al., *Cancer Res.* 53:3092–3097 (1993)). Hybridization to cDNA probes [$\alpha$-$^{32}$P]dCTP-labeled by random priming was performed overnight at 42° C. in 40% formamide, 2 mM EDTA, 900 mM NaCl, 50 mM $Na_2HPO_4$/$NaH_2PO_4$ pH 6.5, 1% sodium dodecyl sulfate, 0.4 g/l polyvinylpyrrolidone, 0.4 g/l Ficoll, 50 g/l dextran sulfate, and 50 mg/l denatured salmon sperm DNA. The nylon membranes were washed twice at room temperature in 2× standard sodium citrate (SSC), 0.1% SDS for 20 min, followed by a last wish under stringent conditions with 0.1×SSC, 0.1% SDS at 56° C. for one hour. The following human cDNA fragments were used as probes: a 1.7 kb EcoRI fragment for stromelysin-3 (Anglard, P., et al., *J. Biol. Chem.* 270:20337–20344 (1995)), a 1.3 kb EcoRI-XbaI fragment for interstitial collagenase and a 1.8 kbL coRI fragment for stromelysin-1 (Muller, D., et al., *Biochem. J.* 253:187–192 (1988)), a 0.7-kb PstI fragment for 36B4 (Masiakowski, P., et al., *Nucleic Acids Res.* 10:7895–7903 (1982)), a 0.6-kb PstI fragment for RAR$\alpha$ and a 0.41-kb XhoI-EcoRI fragment for RAR$\beta$ (Brand, N., et al., *Nature* 332:850–853 (1988)), a 1.3-kb AvaI-BamHI fragment for RAR$\gamma$ (Krust, A., et al., *Proc. Natl. Acad. Sci.* (USA) 86:10–5314 (1989)), and a 1.6 kb XhoI-XbaI fragment for RXR$\alpha$ (Elder, J. T., et al., *J. Invess. Dermatol.* 98:673–679 (1992)). In the case of the RXR$\beta$ probe, a 0.8-kb BamnHI cDNA fragment and a 0.6 kb fragment (nucleotides 1057 to 1677) amplified by polymerase chain reaction were generated from pTLI-hRXR$\beta$ plasmid (Leid, M., et al., *Cell* 08:377–395 (1992)). Similarly, for RXR$\gamma$, a 1.1-kb ApaI-PstI cDNA fragment and a 0.4-kb fragment (nucleotides 356 to 769) amplified by polymerase chain reaction were generated from the pSG5-hRX$\gamma$ plasmid (Mangelsdorf, D. J., et al., *Genes. Dev.* 6:329–344 (1992)). All human RAR and RXR cDNA containing plasmids were kindly provided by P. Kastner (IGBMC; Illkirch Cedex, France). Blots were autoradiographed for 1 to 4 days, and signal quantification was performed using a bio-imaging analyzer (BAS 2000; Fuji Ltd).

Protein Analysis.

Conditioned media from HFL1 fibroblasts were collected and centrifuged in order to eliminate cell debris, followed by a 100-fold concentration by 80% ammonium sulfate precipitation and dialysis against 20 mM Tris-HCl, pH 7.4, 100 mM NaCl, 5 mM $CaCl_2$, 1 $\mu$M $ZnCl_2$, 0.005% Brij-3 5. Protein samples were then separated by SDS-PAGE under reducing conditions, transferred onto nitrocellulose membranes, and revealed with monoclonal antibody 5ST-4C10 against the catalytic domain of stromelysin-3 by using enhanced chemiluminescence (ECL, Amersham) and a peroxidase-coupled anti-mouse IgG (Jackson) (Santavicca, M., et al., *Biochem. J.* 1315:953–958 (1996)).

Nuclear Run-on Transcription Assays.

Control cells and cells treated with 9C-RA (1 $\mu$M) for one to three days were washed twice with ice cold PBS, harvested and centrifuged at 1300 g at 4° C. for 5 min. The pellet was resuspended in 4 ml lysis buffer (10 mM Tris-HCl pH 7.4, 10 mM NaCl, 3 mM $MgCl_2$, 0.5% (v/v) Nonidet P-40), incubated for 5 min on ice and centrifuged at 1300 g at 4° C. for 5 min. This procedure was repeated twice. The final pellet containing the nuclei was resuspended in storage buffer consisting of 50 mM Tris-HCl pH 8.3, 5 mM $MgCl_2$, 0.1 mM EDTA, 40% (v/v) glycerol, and aliquots of $2 \times 10^7$ nuclei were stored at −80° C. before use. In vivo-initiated RNA transcripts from these aliquots were elongated in vitro for 30 min at 30° C. in the presence of 200 $\mu$Ci of [$\alpha$-$^{32}$P]dUTP in a final volume of 200 $\mu$l containing 1 mg/ml heparin, 0.6% (v/v) sarkosyl, 0.4 mM each of ATP, CTP and GTP, 2.5 mM DTT, 0.15 mM PMSF and 350 mM $(NH_4)_2SO_4$. The reaction was stopped by the addition of RNAse-free DNAsel (800 U) in the presence of 1.8 mM $CaCl_2$ for 10 min at 30° C., followed by protein digestion with proteinase K (100 $\mu$g/ml) in 50 mM Tris-HCl pH 7.4, 20 mM EDTA, 1% SDS and incubation (45 to 90 min) at 42° C. until clear samples were obtained. RNA extraction was then performed with phenol/chloroform (1:1, v/v) and the organic phase was further extracted with 10 mM Tris-HCl pH 7.4, 5 mM EDTA, 1% SDS. Pooled aqueous phrases were finally extracted with chloroform and RNA precipitation was carried out at 4° C. for 15 min after the addition of one volume of 20% trichloroacetic acid (TCA) in the presence of 20 $\mu$g tRNA as a carrier. RNA pellets were washed 3 times in 5% TCA and once with 80% ethanol. Dried pellets were then dissolved in hybridization buffer (as described above) to a final specific activity of $5 \times 10^6$ cpm/ml, and hybridized to cDNAs corresponding to human stromelysin-3 (ZIV; Anglard, P., et al., *J. Biol. Chem.* 270:20337–20344 (1995)), human intestinal collagenase (Muller, D., et al., *Biochemn. J.* 253:187–192 (1988)), 36B4 (Masiakowski, P., et al., *Nucleic Acids Res.* 10:7895–7903 (1982)) and the pBluescript II SK+ plasmid. These DNAs were denatured in the presence of 0.3 N NaOH and immobilized onto Hybond nylon membranes (Amersham) by using a slot blot apparatus. Prehybridization at 42° C. for 18 hours and hybridization to in vitro $^{32}$P-labeled elongated RNAs at 42° C. for 3 days were carried out in the same hybridization buffer. Filters were subjected to various washing conditions as follows: twice in 2×SSC, 1% SDS for 15 min at 22° C.; twice in 0.1×SSC, 0.1% SDS for 15 min at 52° C.; once in 2×SSC, in the presence of RNAse A (10 $\mu$g/ml) for 15 min at 37° C.; twice in 2×SSC, 1% SDS for 15 min it 22° C.; and finally, once in 0.1×SSC. 0.1% SDS for 15 min at 52° C. Signal quantification was carried out as described for Northern blot analysis.

CAT Reporter Constructs.

The DR1-tk-CAT, 0.29ST3-CAT, 0.45ST3-CAT. 1.47ST3-CAT and 3.4ST3CAT constructs have been previously described (Anglard, P., et al., *J. Biol. Chem.* 270:20337–20344 (1995)). The $\beta$RARE (DR5)CAT construct (Nagpal, S., et al., *Cell* 70:1007–1019 (1992)) was kindly provided by J.-Y. Chen (IGBMC; Illkirch Cedex, France). The 3.4ST3-CAT-$\Delta$DR1 construct was generated by inserting the 3-kb SphI-XbaI 5'-fragment from the 3.4ST3-CAT construct into the 0.29ST3-CAT construct digested with the same restriction enzymes, thereby deleting a 0.16 kb promoter sequence containing the DR1-RARE that is present at position −385 in the stromelysin-3 gene promoter (Anglard, P., et al., *J. Biol. Chem.* 270:20337–20344 (1995)).

Cell Transfection and CAT Assay.

Human RD rhabdomyosarcoma cells were transiently transfected by the calcium phosphate procedure as previously described (Anglard, P., et al., *J. Biol. Chem.* 270:20337–20344 (1995)), except that the total amount of DNA transfected in each 10 cm-diameter culture dish was made up to 20 $\mu$g with pBluescribe plasmid DNA. For a four-day treatment with RA, cells were first exposed to 1 $\mu$M RA for two days before transfection, whereas for a two-day RA treatment, cells were directly transfected at four hours after plating. In both cases, cells were incubated in the presence of 1 $\mu$M RA for two days after transfection. The $\beta$-galaclosidase expression vector pCH 110 (Pharmacia; Piscataway, N.J.) was used as an internal control to normalize for transfection efficiency. Cell extracts containing four units of $\beta$-galactosidase activity were used for chloramphenicol acetyl transferase (CAT) assays and the reaction products were separated by thin layer chrornatography and visualized by autoradiography. Signal quantification was performed as described for Northern blot analysis.

Example 1

Stimulation of Stromelysin-3 and Inhibition of Interstitial Collagenave RNA Expression by Retinoic Acid in Fibroblasts Since a RARE that conferred ST3 promoter inducibility in COS-1 cells in the presence of RA and its receptors has been previously identified (Anglard, P., et al., *J. Biol. Chem.* 270:20337–20344 (1995)), the question of whether stromelysin-3 gene expression was also regulated by RA in human fibroblasts was evaluated in the present studies. Time course and dose response experiments were performed., and expression of the stromelysin-3 gene was compared to that of interstitial collagenase by Northern blot analysis in HFL1 fibroblasts exposed to 9-cis-RA (9C-RA) in the presence of 5% calf serum.

Figure 2:
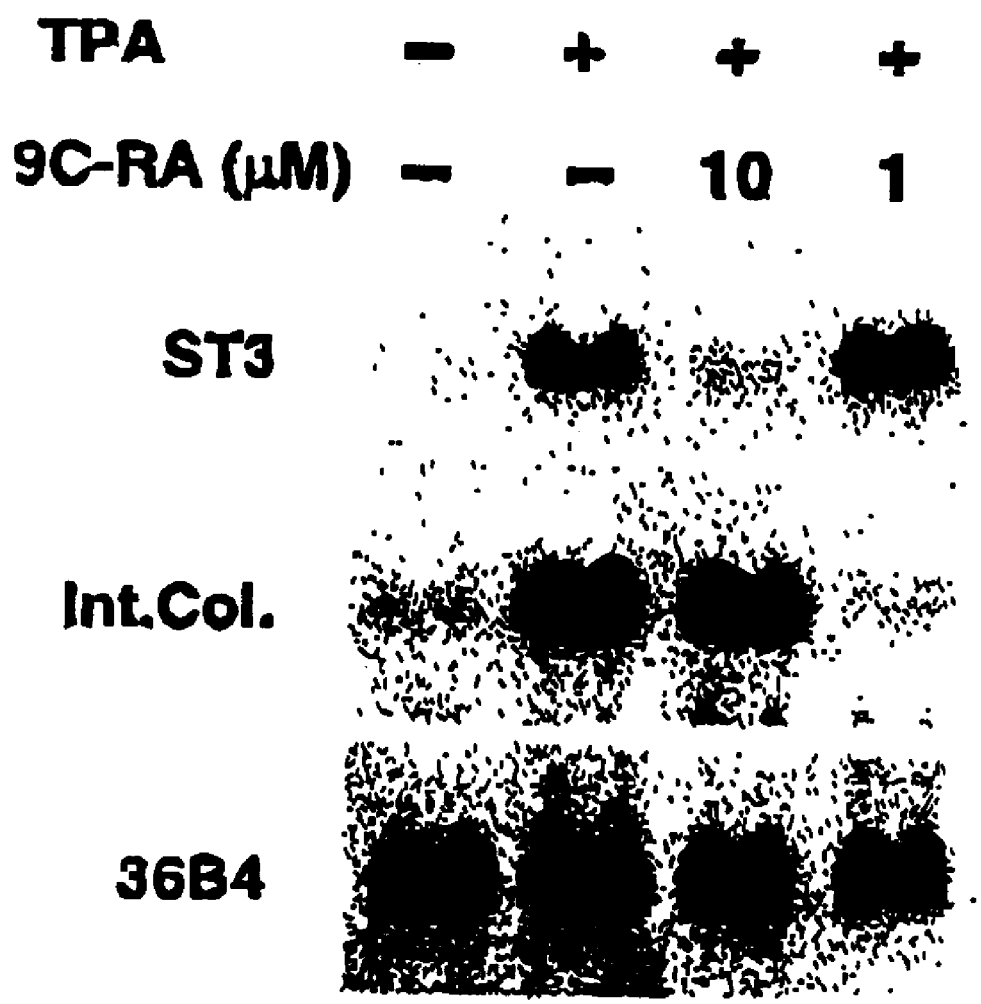
FIG. 2 is an autoradiograph demonstrating the effects of RA treatment on TPA-stimulated stromelysin-3 and interstitial collagenase RNA expression in HFL1 fibroblasts.

As shown in FIG. 1A, in the presence of 1 $\mu$M 9C-RA, stromelysin-3 RNA levels progressively increased from day 1 to day 4, with a 20-fold increase measured after four days of incubation. In contrast, the levels of interstitial collagenas. RNA remained constant when fibroblasts were exposed to RA for one day and rapidly decreased to almost undetectable levels after two days of treatment. When dose response experiments were conducted after incubation during 3.5 days with RA concentrations ranging from 0.1 nM to 1 $\mu$M, the effect of RA was found to be dose-dependent for both genes (FIG. 1B). Nevertheless, the repression of interstitial collagenase expression was much more sensitive to RA treatment than was the induction of the ST3 gene. Indeed, the half-maximal values for stromelysin-3 induction (EC50) and interstitial collagenase repression (IC50) differed by a factor of about 100 (FIG. 1B; EC50~10 nM and IC50 ~0.1 nM). Similar results were obtained by using all-trans-RA (t-RA) instead of 9C-RA, and when the experiments were carried out in serum-free conditions (data not shown). As shown in FIG. 2, however, in the latter case the interstitial collagenase baseline was much lower, hampering analysis of its repression by RA isomers.

These results showing a significant induction of ST3 RNA levels in HFL1 fibroblasts in the presence of RA initially appeared to contradict a recent report using the same fibroblasts as models, wherein it was found that TPA-mediated induction of stromelysin-3 RNA was inhibited by RA (Anderson, I. C., et al., Cancer Res. 55:4120–4126 (1995)). As shown in FIG. 2, however, this inhibition was repeated in the present studies, but only at a concentration of RA of about 10 μM which by far exceeds typical physiological RA concentrations. In addition, this 10 μM RA concentration failed to repress the expression of the interstitial collagenase gene, while this repression was observed at lower, more physiological, RA concentrations, as has been previously noted by others (Yang-Yen, H. F., et al., New Biol. 3:1206–1219 (1991)).

Example 2

Figure 3:
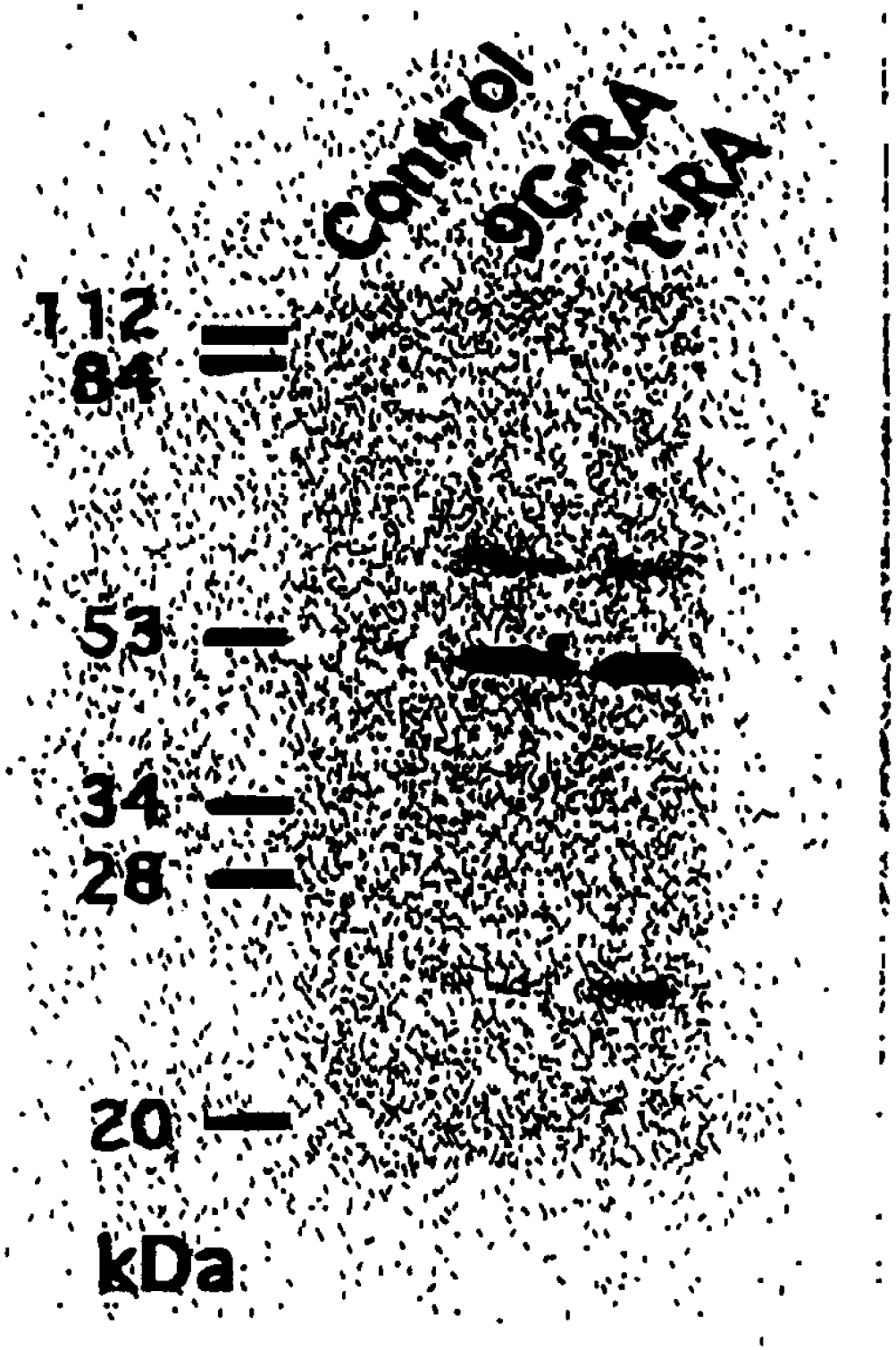
FIG. 3 is a chemiluminograph of a Western blot (using monoclonal antibody 5ST-4C10 raised against the stromelysin-3 catalytic domain) demonstrating the induction of stromelysin-3 synthesis and secretion in HFL1 fibroblasts treated with either 1 μM 9C-RA or 1 μM all-traiis RA (t-RA). Molecular weight markers (kDa) are indicated on the left.

Induction of Stromelysin-3 Protein Synthesis and Secretion by Retinoic Acid in Fibroblasts In order to determine whether stromelysin-3 protein synthesis and/or secretion were also increased by RA treatment, conditioned media from HFL1 fibroblasts were analyzed by Western blot. As demonstrated in FIG. 3, only low levels of the mature form of stromelysin-3 were detected at a molecular weight of about 47 kDa in cells cultured under serum-free conditions. However, when fibroblasts were exposed for three days to 1 μM of either 9C-RA or t-RA, high levels of mature stromelysin-3 were detected together with additional protein species. The highest molecular weight form corresponds to the stromelysin-3 proform, which is known to be converted by furin or furin-like enzymes into the mature form (Pei, D., and Weiss, S. J., Nature 375:244–247 (1995); Santavicca, M., et al., Biochem. J. 315:953–958 (1996)), which in turn can be processed further into another low molecular weight species (FIG. 3).

Example 3

Transcriptional Control of Stromelysin-3 and Interstitial Collagenase Genes by Retinoic Acid in Fibroblasts To determine whether a transcriptional mechanism was involved in controlling the levels of stromelysin-3 and interstitial collagenase RNAs by RA, the nuclear RNAs of both MMPs were analyzed by nuclear run-on assays performed on nuclei isolated from HFL1 fibroblasts treated for one to three days with 1 μM 9C-RA. Radiolabeled RNAs resulting from nascent nuclear RNA transcripts elongated in vitro were hybridized to cDNAs cloned into the pBluescript II SK+ plasmid and corresponding to interstitial collagenase, stromelysin-3, 36B4, or to the plasmid alone as a control for non-specific hybridizati.

Figure 4:
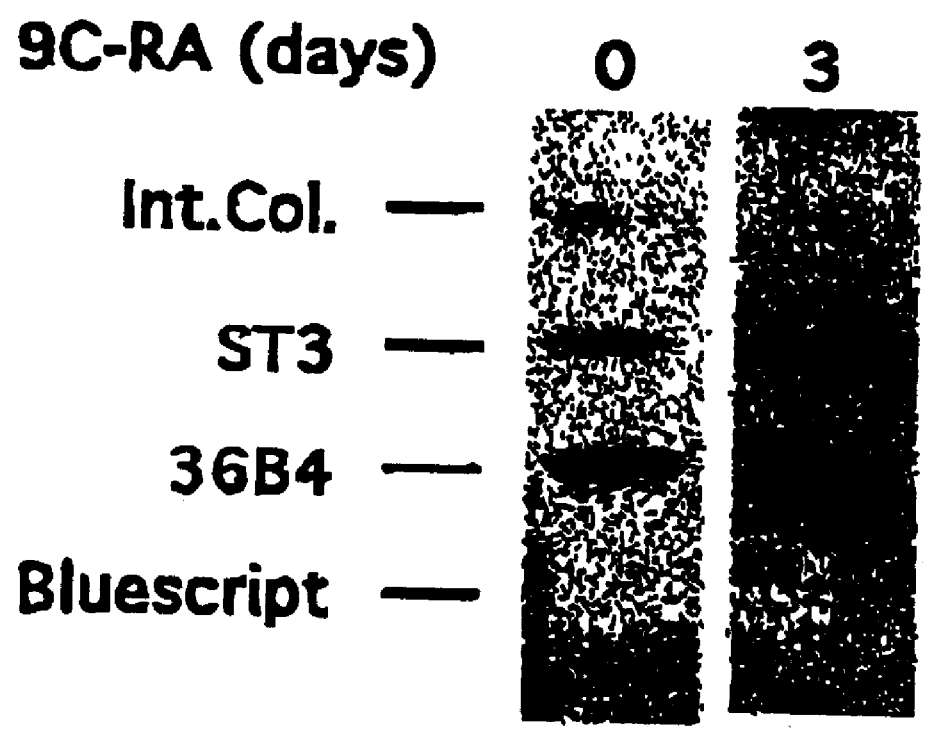
FIG. 4 is an autoradiograph of nuclear run-on transcription assays with nuclei prepared from HFL 1 fibroblasts treated with 9C-RA. Data represent results of one of three independent experiments.

As shown in FIG. 4, both MMP genes are constitutively transcribed in HFL1 fibroblasts. After three days in the presence of RA, interstitial collagenase transcription was no longer detectable. Conversely, RA was found to increase the rate of stromelysin-3 gene transcription twofold, to levels similar to those observed fDr the 36B4 gene whose expression is not affected by RA. Shorter exposure times of HFL1 fibroblasts to RA (one or two days) led to either no, or only minimal, increase in stromelysin-3 gene transcription (data not shown).

Example 4

Activation of the Human Stromelysin-3 Gene Promoter by Retinoic Acid via Endogenous Retinoid Receptors in RD Cells HFL1 fibroblasts, like other non-immortalized human diploid fibroblasts, are difficult to use for promoter studies in transient transfection experiments. Therefore, an established cell line expressing the stromelysin-3 gene was sought to facilitate these transfection studies. Since the stromelysin-3 gene is only weakly expressed in human fibrosarcoma cell lines such as HT-1080 and cannot be induced by TPA in these cells (Okada, A., et al., Proc. Natl. Acad. Sci. USA 92:2730–2734 (1995)), several human cell lines of mesodermal origin were screened for their ability to respond to TPA and RA.

Figure 5:
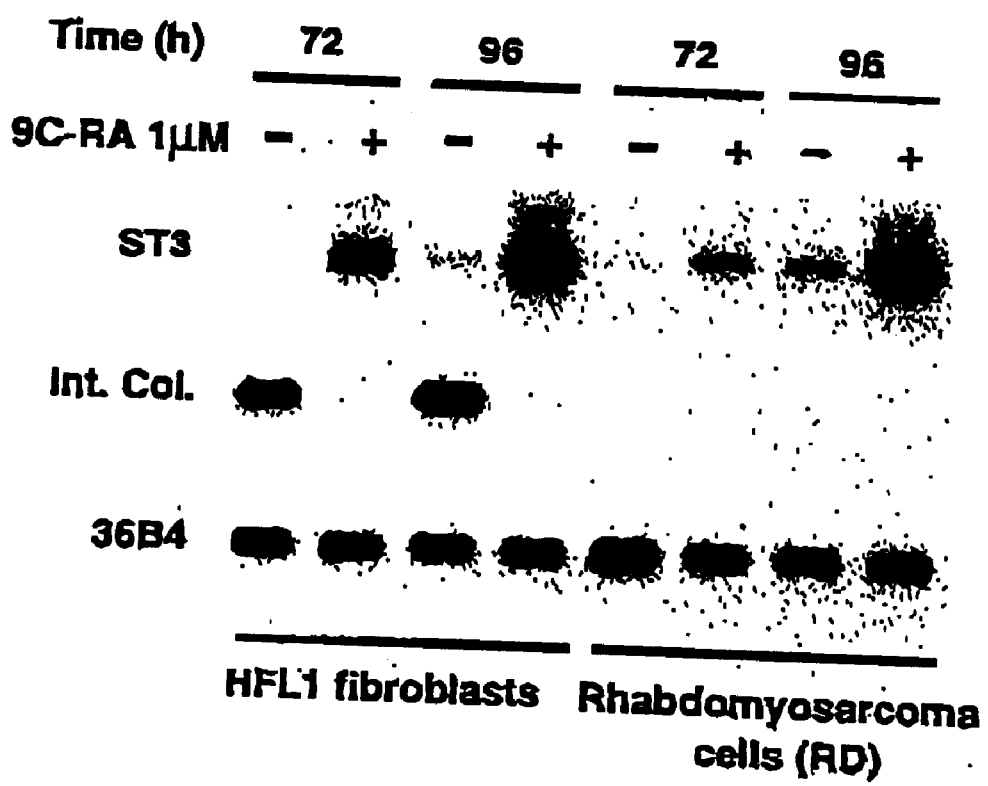
FIG. 5 is an autoradiograph of a Northern blot comparing the expression of stromelysin-3 and interstitial collagenase RNAs in RA-treated HFL1 fibroblasts and RD rhabdomyosarcoma cells.

This screening identified a rhabdomyosarcoma cell line (RD) that exhibits a stromelysin-3 expression pattern very similar to that of HFL1 fibroblasts. For example, as shown in FIG. 5, basal levels of stromelysin-3 RNA expression, as well as its induction by RA which is maximal after four days of incubation, were similar in HFL1 and RD cells. However, RD cells did not express the interstitial collagenase gene, even upon exposure to TPA.

Figure 6:
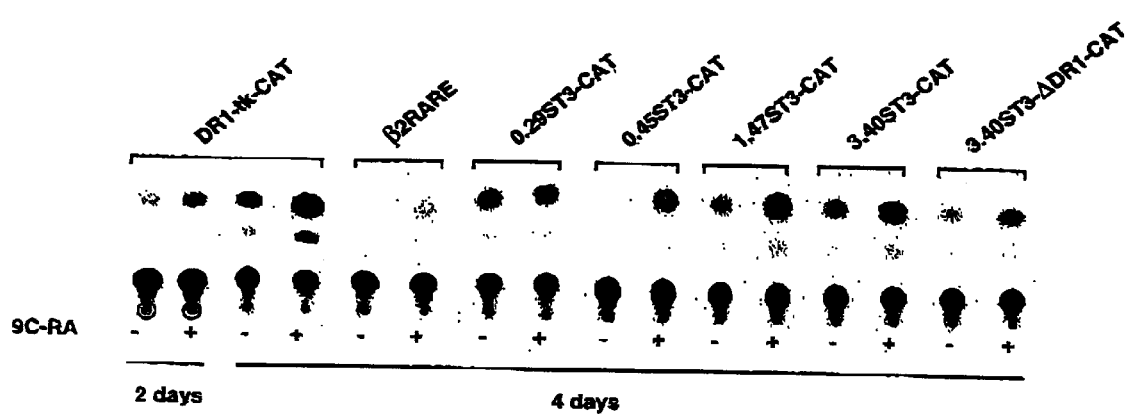
FIG. 6 is a composite autoradiogram comparing ligand-dependent transactivation of the stromelysin-3 gene promoter by various endogenous retinoic acid receptors in RD rhabdomyosarcoma cells transfected with the indicated CAT-reporter plasmids. Data represent results of one of three independent experiments.

In order to further evaluate whether a transcriptional regulation was involved in the induction of stromelysin-3 gene expression by RA, stromelysin-3 promoter activity was analyzed in RD cells exposed to 9C-RA for four days. RD cells that had been preincubated with 9C-RA for two days were transiently transfected by a CAT-reporter gene driven by various lengths of stromelysin-3 promoter and further exposed to RA for an additional period of 2 days, before measurement of CAT activities. As shown in FIG. 6, upon the addition of RA the activities of all three stromelysin-3 promoter constructs containing the DR1-RARE (0.45-, 1.47-, and 3.40-ST3-CAT) were induced 2.8±0.5, 3.2±0.6, and 3.3±0.5 fold (n=3), respectively. Conversely, the absence of the DR1-RARE in the 0.29ST3-CAT and the 3.40ST3-ΔDR1 constructs reduced RA inducibility to 1.2±0.1 and 1.6±0.1 fold (n=3), respectively. A similar remaining activation by RA was previously observed for the 0.29ST3-CAT construct when transfected into COS-1 cells (Anglard, P., et al., J. Biol. Chem. 270:20337–20344 (1995)). This finding may be attributed to the presence of several widely spaced half RARE motifs ($PuG^G/T^{TCA}$) present in this promoter region and which have been shown to activate transcription in the presence of RA (Kato, S., et al., Mol. Cell Biol. 15:5858–5867 (1995)). The activation by RA was also tested on the RARβ2 promoter, which contains a RARE of the DR5 type (Nagpal, S., et al., Cell 70:1007–1019 (1992)), and on the isolated DR1 element inserted upstream of the herpes simplex virus thymidine kinase (tk) promoter. The activity of these two constructs was induced 3.1±0.2. and 4.9±0.7 fold (n=3) by RA, respectively, thus to levels comparable to those observed for ST3 constructs. However, the transactivation of the DR1-tk-CAT construct was weaker (1.4±0.3 fold, n=2) when RD cells were exposed to RA for only two instead of four days, thereby suggesting, that some of the regulatory factors implicated in this activation are not constitutively expressed in RD cells. Since these experiments were performed without the cotransfection of any retinoid receptor, it is clear that the observed effects were mediated through endogeneous RA receptors.

Example 5

Retinoic Acid Receptor Expression in Fibroblasts

Figure 7:
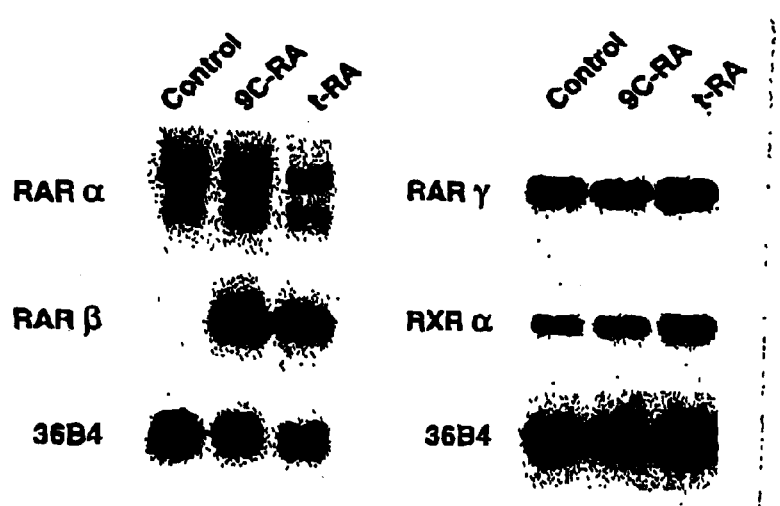
FIG. 7 is an autoradiograph of a Northern blot demonstrating the expression of RARs and RXRs in HFL1 fibroblasts treated with 1 μM 9C-RA or t-RA for 3 days. Autoradiographs were exposed for 16 hours (RXRα), 1.5 days (RARα and RARγ), 3 days (RARβ) and 4 hours (36B4).

To determine the respective contribution of RARs and RXRs in mediating stromelysin-3 induction and interstitial collagenase repression by RA, their expression in HFL1 fibroblasts was first analyzed by Northern blot. As shown in FIG. 7, untreated fibroblasts cultured in serum-free conditions expressed similar levels of RARα, RARγ and RXRα RNAs, with steady state levels relatively constant over the time of culture (not shown). No expression was detected in untreated zells for RARβ, RXRβ and RXRγ RNAs, however, even when up to 30 μg of total RNA were loaded for analysis (FIG. 7). These results are consistent with recent studies that have shown that RARα, RARγ and RXRα are the predominant receptors expressed in human skin (Fisher, G. J., et al., *J. Biol. Chem.* 265:20629–20635 (1994)), as well as in various human cell lines (Pan, L., et al, *J. Cell Biochem.* 57:575–589 (1995); Lotan, R., et al., *Cancer Res.* 55:232–236 (1995); Agarwal, C., *Cell Growth Differ.* 7:521–530 (1996)). The expression of RXRα, was only slightly increased (less than twofold) in cells treated with either 9C-RA or t-RA, whereas RARα and RARγ levels remained unaffected. In contrast, RARβ RNA levels increased from undetectable to high levels in cells exposed to either of the RA isomers (FIG. 7). Similar results were obtained in fibroblasts cultured in 5% calf serum, although RARβ was induced to a lower extent in these cells than in cells cultured under serum-free conditions (data not shown).

Example 6

Synergistic Activation of Stromelysin-3 Gene and Repression of Interstitial Collagenase Gene by Specific Synthetic Retinoids Having demonstrated the effects of RA on induction of the expression of the stromelysin-3 gene, and on the repression of the expression of the interstitial collagenase gene, it was asked whether the ligand-dependent activation of both RARs and RXRs was required for these effects. These studies used the synthetic ligands Am80 (Hashimoto, Y., et al., *Biochem. Biophys. Res. Commun.* 166:1300–1307 (1990)) and CD666 (Bernard, B.A., et al., *Biochem. Biophys. Res. Commun.* 186:977–983 (1992)), which at appropriate concentrations selectively activate RARα and RARγ, respectively (Taneja, R., et al., *Proc. Natl. Acad. Sci. USA* 93:6197–6202 (1996)); BM753, a pure RARα agonist (Chen, J.-Y., et al., *Nature* 382:819–822 (1996)), and BM649, an RXR (α,β,γ)-selective agonist (Lehmann, J. M., et al., *Science* 258:1944–1946 (1992)). The expression levels of stromelysin-3 and interstitial collagenase RNAs in retinoid-treated HFL1 cells were evaluated after 3.5 days of cell culture in the presence of these synthetic retinoids and compared to those observed in the presence of 9C-RA and t-RA.

Figure 8:
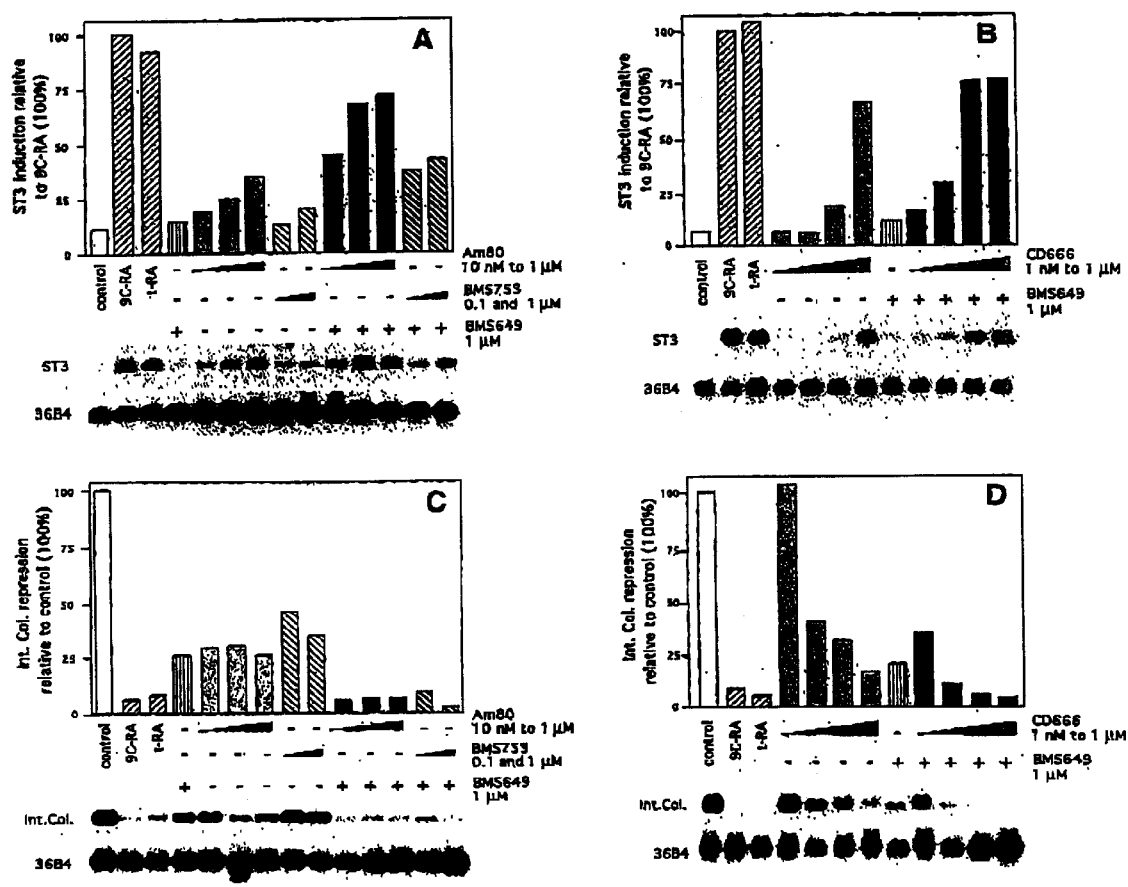
FIGS. 8A–8D are a composite of autoradiographs, and histograms of phosphorImager scanning of the autoradiograms, comparing the expression of stromelysin-3 (FIGS. 8A and 8B) and interstitial collagenase (FIGS. 8C and 8D) genes in HFL1 fibroblasts treated for 3.5 days with RARα- (Am80 and BMS753.
Figure 9:
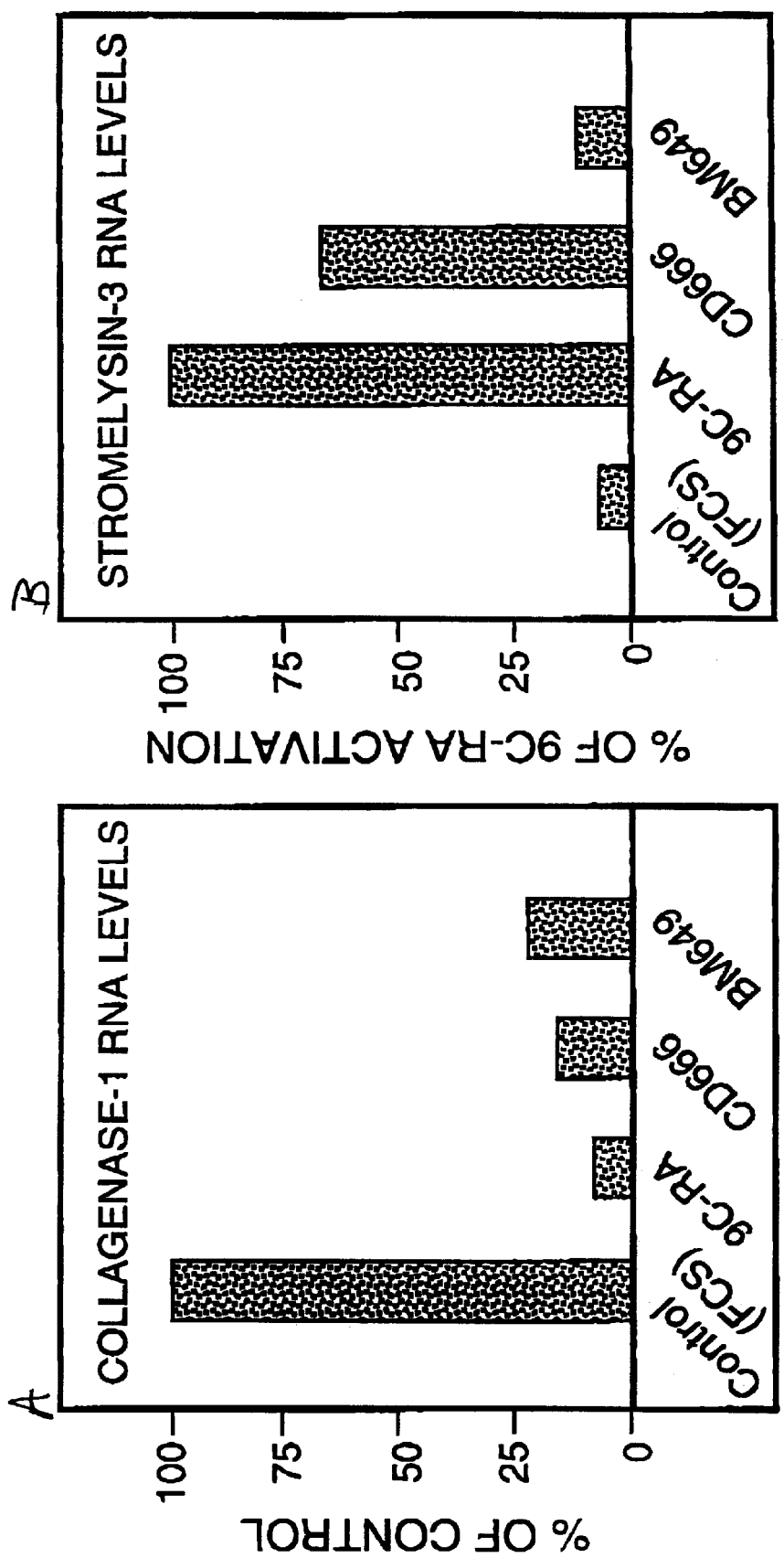
FIGS. 9A–9B are a bar graph demonstrating the effects of the retinoids 9-cis-RA (9C-RBA), CD666 and BMS649 (BM649) on the expression of the collagenase-1 (FIG. 9A) and stromelysin-3 (FIG. 9B) genes in HFL1 fibroblasts. Retinoids were used at a concentration of 1 μM each.
Figure 10:
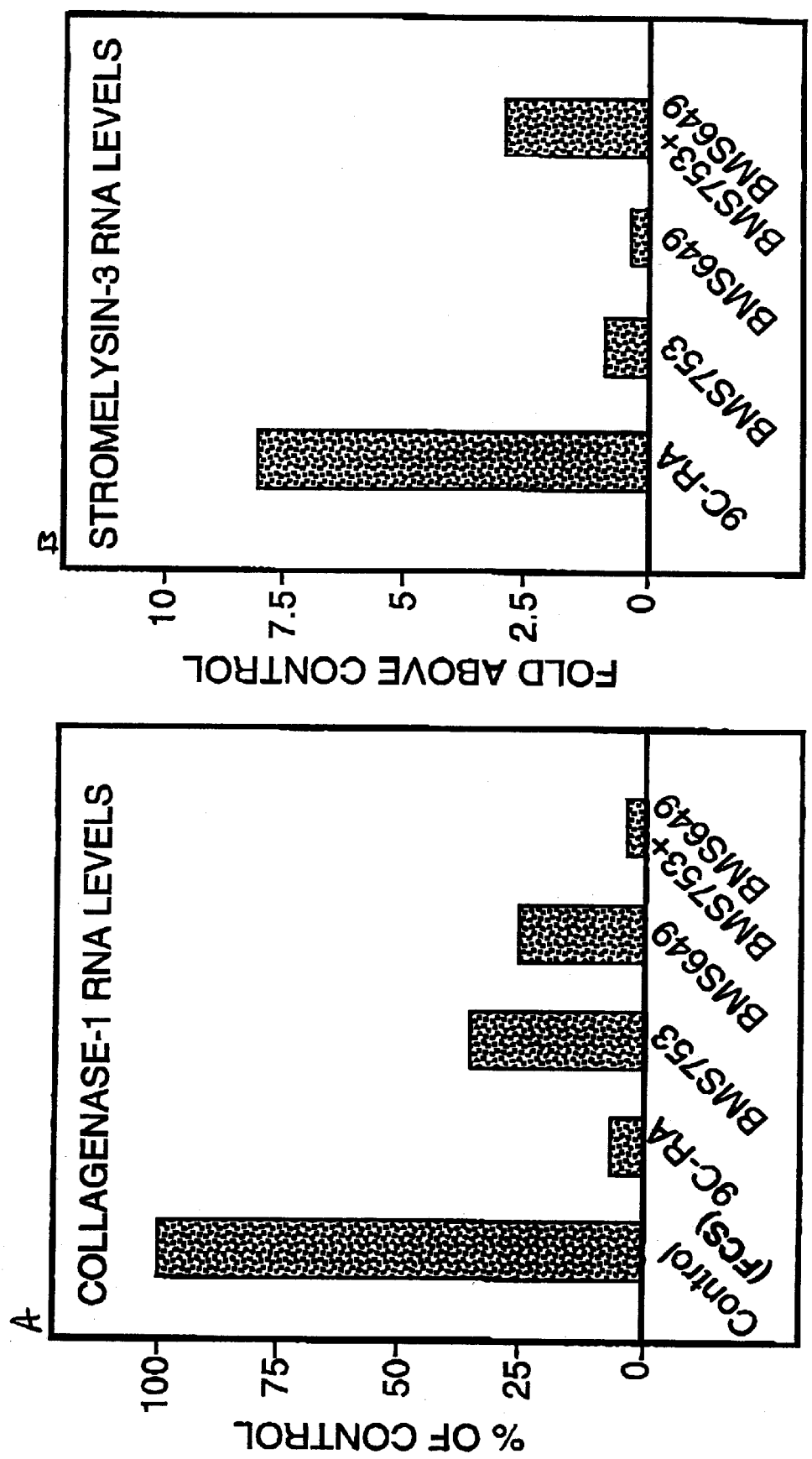
FIGS. 10A–10B are a bar graph demonstrating the effects of the synthetic RARα agonist BMS753 and the synthetic RXR agonist BMS649 on the expression of the collagenase-1 (FIG. 10A) and stromelysin-3 (FIG. 10B) genes in HFL1 fibroblasts. Retinoids were used at a concentration of 1 μM each.

As shown in FIG. 8, using these retinoids individually at low and/or selective concentrations, either no or only minimal induction of stromelysin-3 was detected (FIGS. 8A and 8B), while interstitial collagenase expression was reduced by at least 50% (FIGS. 8C and 8D). At higher concentrations (>10 nM), where Am80 and CD666 lose their specificity and act as pan-RAR agonists (Taneja, R., et al., *Proc. Natl. Acad. Sci. USA* 93:6197–6202 (1996)), higher levels of stromelysin-3 RNA were observed, while interstitial collagenase expression was repressed further. Interestingly, very little stromelysin-3 gene induction was observed in cells treated with the pure RARα agonist BM753 or the pan-RXR agonist B4649, even when these retinoids were used at a 1 μM concentration (FIGS. 9A and 9B). In marked contrast, the combination of either Am80 (100 nM and 1 μM) or CD666 (100 nM) with the pan-RXR ligand BM649 (1 μM) resulted in a synergistic induction of the stromelysin-3 gene, reaching expression levels close to those observed with the natural ligands. A synergistic effect was also observed when the BM753 and BM649 ligands were combined, although the expression levels of stromelysin-3 RNA did not exceed 50% of those observed in the presence of the natural ligands (FIGS. 10A and 10B). However, any of these combinations was found to fully repress interstitial collagenase gene expression. Stromelysin-1 gene expression was similarly repressed in HFL1 fibroblasts (data not shown), suggesting that the retinoids used in the present studies may efficiently repress the expression of any AP1-regulated MMP.

Taken together, the present observations indicate that while the selective activation of either RARα or RARγ or RXRs substantially repress interstitial collagenase gene expression, the combination of RARs and RXRs is required for optimal stromelysin-3 gene induction and for fill repression of interstitial collagenase.

General Discussion

It has previously been shown that the stromelysin-3 gene promoter differed from most other MMP promoters by the absence of a functional AP1 binding site and the presence of a RARE in its proximal region. In the present study, the regulation of stromelysin-3 gene expression by RA was further investigated and this expression was compared to that of interstitial collagenase, another MMP. Stromelysin-3 and interstitial collagenase are both predominantly expressed by stromal cells of human carcinomas (MacDougall, J. R., and Matrisian, L. M., *Canc. Metast. Rev.* 14:351–362 (1996)), and their high expression levels were found to be associated with a poor clinical outcome in some carcinomas (Engel, G., et al., *Int. J. Cancer* 58:830–835 (1994); Chenard, M.-P., et al. *Int. J. Cancer* 69(6)):448–451 (1996); Murray, G. I., et al., *Nat. Med.* 2:461–462 (1996)). Considering that retinoids by themselves, or when associated with other drugs such as tamoxifen, are regarded as potential new anticancer agents (Abrams, J. S., et al., *Cancer* 94:1164–1176(1994); Sporn, M. B., *Lancet* 347:1377–1381 (1996); Costa, A., et al., *Am. Assoc. Cancer Res.* 37:655–5656 (1996)), it is important to elucidate the mechanisms by which the expression of MMPs implicated in cancer progression is regulated by RA. In the present invention, it has been demonstrated that both natural RA isomers, 9C-RA and t-RA strongly induce stromelysin-3 RNA and protein expression and simultaneously repress interstitial collagenase expression in human fibroblasts. In addition, the present results demonstrate that both genes are controlled by RA through a transcriptional mechanism, and that RAR-RXY heterodimers are likely to be the functional units required for optimal control of these genes by RA.

AP1 and retinoid receptors are regarded as effectors of opposite pathways of cell proliferation and differentiation, and they are mutually antagonistic at the level of transactivation and DNA binding (Fanjul, A., et al., *Nature* 372:107–111 (1994), Yang-Yen, H. F., et al., *New. Biol.* 3:1206–1219 (1991); Pfahl, M., *Endocr. Rev.* 14:651–658 (1993); Chen, J. Y., et al., *EMBO J.* 14:1187–1197 (1995)). Indeed, MMP genes containing an AP1 binding site in a conserved position in their promoter, or other genes like those for TGF-β1 (Salbert, G., et al., *Mol Endocrinol.* 7:1347–1356 (1993)) and IL-6 (Zitnik, R. J., et al., *J. Immuol.* 152:1419–1427 (1994)), are TPA-inducible, while their expression is inhibited by RA. Since AP1 can reciprocally inhibit transactivation by RARs and RXRs, the observation that the stromelysin-3 gene is induced by both TPA and RA in a given cell type is quite unexpected and represents an unusual example of a gene uprngulated by both agents.

In the present invention, it has further been found that physiological concentrations of RA efficiently induce both the expression of the stromelysin-3 gene and the repression of the interstitial collagenase gene in HFL1 human fibroblasts, the latter being observed at RA concentrations lower than those necessary for stromelysin-3 induction. Interestingly, the IC50 for interstitial collagenase and the EC50 for stromelysin-3 reported here are very similar to the those recently reported in promoter studies (Chen, J. Y., et al., *EMBO J.* 14:1187–1197 (199.5)), wherein it was shown that the repression of AP1-induced transcription from the interstitial collagenase promoter was about 100 times more sensitive to RA treatment than was the transactivation of a RARE-tk-CAT construct. These observations suggesting that the regulation of both genes by RA may be achieved through a transcriptional mechanism were further evaluated here by measuring the transcriptional rate of both genes in HFL1 fibroblasts in run-on assays. In the presence of RA, a complete inhibition of interstitial collagenase transcription was observed; this inhibition is likely to result from an RAR/AP1 interaction, as has been previously documented (Pfahl, M., *Endocr. Rev.* 14:651–658 (1993); Nagpal, S., et al., *J. Biol. Chem.* 270:923–927 (1995)). On the other hand, a twofold increase in the stromelysin-3 gene transcriptional rate was found when HFL1 fibroblasts were exposed to RA for three days, while no clear transcriptional activation could be detected for shorter exposure times. Although it is difficult to determine whether this twofold increase can fully account for the 20-fold increase in stromelysin-3 RNA levels observed after four days of RA treatment, it should be noted that run-on studies with other RA-inducible genes containing a RARE in their promoter exhibited similar profiles. Thus, the RARβ and the laminin B1 RNAs were found to be induced at high levels by RA in F9 cells, while no, or only a moderate, increase in transcriptional rates could be detected for these genes by nuclear run-on assays (Hu, L., & Gudas, L. J., *Mol. Cell Biol.* 10:391–396 (1990); Wang, S. Y., et al., *Dev. Biol.* 107:75–86 (1985)). In all instances, the contribution of a transcriptional mechanism in stromelysin-3 gene induction is further supported by the finding that RA induces stromelysin-3 promoter activity in RD cells. By analyzing various lengths of this promoter in transient transfection experiments, a threefold induction of stromelysin-3 promoter activity was observed in the presence of 9C-RA; this induction was strongly reduced in the constructs lacking the DR1-RARE. Interestingly, this transactivation was observed without addition of retinoid receptors, indicating that the DR1-RARE was activated by functional endogenous retinoid receptors in these cell.

Previous studies have shown that while all RARs could potentially mediate the induction of RA target genes, the involvement of a given receptor was dependent on many parameters including promoter context or cell type (Nagpal, S., et al., *Cell* 70:1007–1019 (1992); Taneja, R., et al., *Proc. Natl. Acad. Sci. USA* 93:6197–6202 (1996)). When the expression of RARs and RXRs was evaluated in HFL-1 fibroblasts in the present invention, RARα, RARγ and RXRα RNAs were found to be constitutively expressed at high levels. In contrast, no RNA could be detected for RXRβ and RXRγ, while that for RARβ was strongly induced from barely detectable levels in untreated fibroblasts to high levels in the presence of 9C- or t-RA. Similar observations have been made in fibroblasts from human dermis (Lee, X., et al., *Mol Carcinog.* 8:112–122 (1993)) and lung (van der Leede, B. M., et al., *Mol Carcinog.* 8:112–122 (1993)).

The suggestion that specific retinoid receptors might be involved in the regulation of stromelysin-3 and interstitial collagenase expression by RA in HFL1 fibroblasts was tested here by examining the expression of both genes in the presence of selective retinoids. These retinoids, when used individually at concentrations at which they selectively activate a given RAR (Am80, CD666, BM753), or all three RXRs (BM649), led to no, or only very weak, induction of the stromelysin-3 gene, while they repressed interstitial collagenase expression by at least 50%. In marked contrast, a clear induction of the stromelysin-3 gene was observed when any of the selective RAR ligands was used in combination with the BM649 RXR-specific ligand. It should be noted, however, that the combination BM753-BM4649 (RARα-RXRs) was less efficient than the other combinations. Since stronger inductions were observed by combining the BM649 RXR agonist with either Am80 or CD666 at concentrations at which they both promiscuously activate all three RARs, it is reasonable to believe that either RARβ and/or RARγ could interact with RXRs for an optimal stromelysin-3 induction. Consistent with the notion that RXRα seems to be the major RXR expressed in fibroblasts, it can be concluded from the present results that the two heterodimers RARβ and/or RARγ-RXRα are likely to represent the functional units required to induce the expression of the stromelysin-3 gene at physiological RA concentrations. This possibility is also consistent with in vitro studies which have shown that heterodimers bind to RARE much more efficiently than do the respective homodimers (Glass, C. K., *Endocr. Rev.* 15:391–407 (1994); Giguere, V., *Endocr. Rev.* 15:61–79 (1994)). In this respect, it is noteworthy that the activation of a single RAR or RXR was shown here to be sufficient to substantially repress interstitial collagenase expression in HFL1 fibroblasts, but that the activation of both partners of heterodimers was necessary for a full repression.

In summary, while transcription studies have demonstrated that RA regulates the expression of target genes by either activating RAREs or repressing AP1 activity, the present studies have examined the regulation of two genes belonging to the MMP family and have shown that they are differentially regulated by RA in luman fibroblasts. Indeed, it has been shown here that physiological concentrations of RA induce stromelysin-3 expression but repress interstitial collagenase expression. Compared to the repression of interstitial collagenase, stromelysin-3 gene induction relies on more restricted conditions based on a lower sensitivity to both natural and synthetic retinoids, and on a more restricted receptor requirement involving RAR/RXR heterodimers. In contrast, a substantial transcriptional repression of interstitial collagenase is achieved by retinoids activating only one type of receptors, although the involvement of RAR/RXR heterodimers is required for a full repression.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of treating a mammal suffering from or predisposed to a physical disorder, comprising administering to said mammal an effective amount of a pharmaceutical composition comprising at least one retinoic acid receptor (RAR) agonist and at least one retinoid X receptor (RXR) agonist, wherein said at least one RAR agonist and said at least one RXR agonist are different compounds, and a pharmaceutically acceptable carrier or excipient therefor, wherein said composition differentially modulates the expression of a first matrix metalloproteinase gene comprising at least one AP1-binding site and a second mammalian matrix metalloproteinase gene comprising at least one retinoic acid response element (RARE).

2. The method of claim 1, wherein said physical disorder is selected from the group consisting of a carcinoma, arthritis, osteoporosis, multiple sclerosis, atherosclerosis, corneal ulceration and diabetic retinopathy.

3. The method of claim 1, wherein said first matrix metalloproteinase gene is an interstitial collagenase gene and said second matrix metalloproteinase gene is a stromelysin-3 gene.

4. The method of claim 1, wherein said RXR agonist is a pan-RXR agonist.

5. The method of claim 1, wherein said RAR agonist is a RARα agonist.

6. The method of claim 1, wherein said composition inhibits the expression of said first mammalian matrix metalloproteinase gene.

7. The method of claim 1, wherein said physical disorder is a cancer.

8. The method of claim 4, wherein said pan-RXR agonist is BMS649.

9. The method of claim 5, wherein said RARα agonist is BMS753.

10. A method of treating a mammal suffering from or predisposed to a physical disorder, comprising administering to said mammal an effective amount of a pharmaceutical composition comprising at least one RAR agonist and at least one RXR agonist, wherein said at least one RAR agonist and said at least one RXR agonist are different compounds, and a pharmaceutically acceptable carrier or excipient therefor, wherein said composition inhibits the expression of an interstitial collagenase gene in said mammal.

11. The method of claim 10, wherein said RAR agonist is an RARα agonist.

12. The method of claim 10, wherein said RXR agonist is a pan-RXR agonist.

13. The method of claim 10, wherein said physical disorder is selected from the group consisting of a carcinoma, arthritis, osteoporosis, multiple sclerosis, atherosclerosis, corneal ulceration and diabetic retinopathy.

14. The method of claim 10, wherein said physical disorder is a cancer.

15. The method of claim 11, wherein said RARα agonist is BMS753.

16. The method of claim 12, wherein said pan-RXR agonist is BMS649.

17. A method of treating a human suffering from or predisposed to a physical disorder, comprising administering to said human an effective amount of a pharmaceutical composition comprising at least one RAR agonist and at least one RXR agonist, wherein said at least one RAR agonist and said at least one RXR agonist are different compounds, and a pharmaceutically acceptable carrier or excipient therefor, wherein said composition inhibits the expression of an interstitial collagenase gene in said human.

18. The method of claim 17, wherein said RAR agonist is an RARα agonist.

19. The method of claim 17, wherein said RXR agonist is a pan-RXR agonist.

20. The method of claim 17, wherein said physical disorder is selected from the group consisting of a carcinoma, arthritis, osteoporosis, multiple sclerosis, atherosclerosis, corneal ulceration and diabetic retinopathy.

21. The method of claim 17, wherein said physical disorder is a cancer.

22. The method of claim 18, wherein said RARα agonist is BMS753.

23. The method of claim 19, wherein said pan-RXR agonist is BMS649.

* * * * *